(12) United States Patent  
Kniep et al.

(10) Patent No.: US 8,702,991 B2  
(45) Date of Patent: Apr. 22, 2014

(54) ELECTRICAL MICROORGANISM AGGREGATION METHODS

(71) Applicant: Heliae Development, LLC, Gilbert, AZ (US)

(72) Inventors: Justin S. Kniep, Chandler, AZ (US); Aniket Kale, Gilbert, AZ (US)

(73) Assignee: Heliae Development, LLC, Gilbert, AZ (US)

( * ) Notice: Subject to any disclaimer, the term of this patent is extended or adjusted under 35 U.S.C. 154(b) by 0 days.

(21) Appl. No.: 13/899,769

(22) Filed: May 22, 2013

(65) Prior Publication Data

US 2014/0017756 A1    Jan. 16, 2014

Related U.S. Application Data

(63) Continuation-in-part of application No. 13/733,217, filed on Jan. 3, 2013.

(60) Provisional application No. 61/670,888, filed on Jul. 12, 2012, provisional application No. 61/707,249, filed on Sep. 28, 2012.

(51) Int. Cl.  
*C02F 1/463* (2006.01)

(52) U.S. Cl.  
USPC ............... 210/712; 44/605; 47/1.4; 204/571; 210/709; 210/738; 210/748.01; 210/805

(58) Field of Classification Search  
CPC .............. C02F 1/30; C02F 1/305; C02F 1/46; C02F 1/461; C02F 1/146104; C02F 1/46109; C02F 1/463; B01D 57/02; B03C 5/00; B03C 5/02

USPC ............... 44/307, 308, 605; 422/20; 210/702, 210/712, 738, 748.01, 748.02, 748.03, 764, 210/805, 739, 744, 709; 204/450, 554, 563, 204/571; 435/134, 157, 160, 161, 257.1, 435/261; 47/1.4

See application file for complete search history.

(56) References Cited

U.S. PATENT DOCUMENTS 2,171,490 A    8/1939   Dalpayrat  
4,055,491 A   10/1977   Porath-Furedi  
(Continued)

FOREIGN PATENT DOCUMENTS

WO        9707065 A1     2/1997  
WO     2007114528 A1    10/2007  
(Continued)

OTHER PUBLICATIONS

Huang et al., Acoustic separation of liquid hydrocarbons from wastewater, United States Statutory Invention Registration, Aug. 6, 1996.

(Continued)

*Primary Examiner* — Joseph Drodge  
(74) *Attorney, Agent, or Firm* — Len Smith, Esq.; Justin Kniep, Esq.; Wilmer Cutler Pickering Hale and Dorr LLP

(57) ABSTRACT

Described herein are systems, methods, and apparatuses for aggregating microorganism in an aqueous suspension. In particular, are systems, methods, and apparatuses that apply an electrical field to an aqueous suspension comprising microorganisms as the aqueous suspension follows a flow path to cause aggregation of the microorganisms. The electrical field may be continuous or pulsed. In some embodiments, the flow path for the aqueous suspension may vary.

7 Claims, 21 Drawing Sheets

(56) References Cited

U.S. PATENT DOCUMENTS

| | | | |
|---|---|---|---|
| 4,107,026 A | 8/1978 | Freeman | |
| 4,168,222 A | 9/1979 | Freeman | |
| 4,170,529 A | 10/1979 | Freeman | |
| 4,207,158 A | 6/1980 | Freeman | |
| 4,236,349 A * | 12/1980 | Ramus | 47/1.4 |
| 4,292,408 A | 9/1981 | Zimmermann et al. | |
| 4,561,953 A | 12/1985 | Muralidhara et al. | |
| 4,802,964 A | 2/1989 | Muralidhara et al. | |
| 4,861,496 A | 8/1989 | Diaz | |
| 4,971,705 A | 11/1990 | Roslonski | |
| 4,983,189 A * | 1/1991 | Peterson et al. | 210/748.02 |
| 5,019,230 A | 5/1991 | Candor | |
| 5,020,977 A | 6/1991 | Lucas | |
| 5,043,048 A | 8/1991 | Muralidhara | |
| 5,049,248 A | 9/1991 | Muralidhara et al. | |
| 5,064,515 A | 11/1991 | Harapanahalli | |
| 5,075,012 A | 12/1991 | Busse | |
| 5,098,538 A | 3/1992 | Kim et al. | |
| 5,230,809 A | 7/1993 | Roslonski | |
| 5,259,940 A | 11/1993 | Candor | |
| 5,292,421 A | 3/1994 | Senapati et al. | |
| 5,326,530 A | 7/1994 | Bridges | |
| 5,344,533 A | 9/1994 | Candor | |
| 5,344,535 A | 9/1994 | Betts | |
| 5,362,371 A | 11/1994 | Candor | |
| 5,403,455 A | 4/1995 | Candor | |
| 5,435,893 A | 7/1995 | Sun et al. | |
| H1568 H | 8/1996 | Huang | |
| 5,593,565 A | 1/1997 | Ajdari | |
| 5,653,859 A * | 8/1997 | Parton et al. | 204/450 |
| 5,695,650 A | 12/1997 | Held | |
| 5,711,888 A | 1/1998 | Trampler | |
| 5,891,342 A | 4/1999 | Tije | |
| 5,893,979 A | 4/1999 | Held | |
| 6,030,538 A | 2/2000 | Held | |
| 6,325,916 B1 | 12/2001 | Lambert et al. | |
| 6,326,177 B1 | 12/2001 | Schoenbach et al. | |
| 6,524,486 B2 | 2/2003 | Borodyanski et al. | |
| 6,871,744 B2 | 3/2005 | Miller et al. | |
| 6,881,314 B1 | 4/2005 | Wang | |
| 7,001,520 B2 | 2/2006 | Held et al. | |
| 7,340,957 B2 | 3/2008 | Kaduchak et al. | |
| 7,347,923 B2 * | 3/2008 | Cummings et al. | 204/547 |
| 7,462,287 B2 | 12/2008 | Berrak et al. | |
| 7,507,341 B2 | 3/2009 | Gallagher et al. | |
| 7,572,369 B2 | 8/2009 | Gallagher et al. | |
| 7,572,623 B2 | 8/2009 | Mangano | |
| 7,578,918 B2 | 8/2009 | Berrak et al. | |
| 7,645,382 B2 | 1/2010 | Gallagher et al. | |
| 7,695,621 B2 | 4/2010 | Gallagher et al. | |
| 7,730,558 B2 | 6/2010 | Choe | |
| 7,828,953 B2 | 11/2010 | Berrak et al. | |
| 7,837,040 B2 | 11/2010 | Ward et al. | |
| 7,931,784 B2 * | 4/2011 | Medoff | 204/157.63 |
| 7,943,031 B2 | 5/2011 | Jones et al. | |
| 7,950,181 B2 | 5/2011 | McCall | |
| 7,998,225 B2 * | 8/2011 | Powell | 44/308 |
| 8,083,068 B2 | 12/2011 | Kaduchak et al. | |
| 8,227,257 B2 | 7/2012 | Ward et al. | |
| 8,425,749 B1 | 4/2013 | Ravula | |
| 2003/0150789 A1 | 8/2003 | Miller et al. | |
| 2003/0159932 A1 | 8/2003 | Betts | |
| 2004/0079650 A1 | 4/2004 | Morkovsky et al. | |
| 2005/0016870 A1 | 1/2005 | Berrak et al. | |
| 2005/0199499 A1 | 9/2005 | Berrak et al. | |
| 2006/0269531 A1 | 11/2006 | Beebe et al. | |
| 2007/0048859 A1 | 3/2007 | Sears | |
| 2007/0227904 A1 | 10/2007 | Miller et al. | |
| 2008/0044891 A1 | 2/2008 | Kinley et al. | |
| 2009/0090673 A1 | 4/2009 | Jensen et al. | |
| 2009/0181438 A1 * | 7/2009 | Sayre | 435/134 |
| 2009/0206171 A1 | 8/2009 | Friend | |
| 2010/0078384 A1 | 4/2010 | Yang | |
| 2010/0078389 A1 | 4/2010 | Elektorowicz et al. | |
| 2010/0116686 A1 | 5/2010 | Wiemers et al. | |
| 2010/0129559 A1 | 5/2010 | Dermoune et al. | |
| 2010/0163428 A1 | 7/2010 | Dermoune et al. | |
| 2010/0236931 A1 | 9/2010 | Fernando | |
| 2010/0261918 A1 | 10/2010 | Chianelli et al. | |
| 2010/0314323 A1 | 12/2010 | Lean et al. | |
| 2011/0003350 A1 * | 1/2011 | Schafran et al. | 435/134 |
| 2011/0086386 A1 | 4/2011 | Czartoski et al. | |
| 2011/0095225 A1 | 4/2011 | Eckelberry et al. | |
| 2011/0123392 A1 | 5/2011 | Dionne et al. | |
| 2011/0127164 A1 | 6/2011 | Sinha et al. | |
| 2011/0262990 A1 | 10/2011 | Wang et al. | |
| 2012/0040428 A1 | 2/2012 | Reep et al. | |
| 2012/0055797 A1 | 3/2012 | Dermoune et al. | |
| 2012/0091000 A1 | 4/2012 | Cook | |
| 2012/0095245 A1 * | 4/2012 | Lane et al. | 554/8 |
| 2012/0129244 A1 * | 5/2012 | Green et al. | 435/257.1 |
| 2012/0193297 A1 | 8/2012 | Lean | |
| 2012/0205257 A1 | 8/2012 | Collier | |
| 2012/0295338 A1 | 11/2012 | Reep et al. | |
| 2012/0325727 A1 | 12/2012 | Dionne | |
| 2012/0328477 A1 | 12/2012 | Dionne | |
| 2012/0329121 A1 | 12/2012 | Green | |
| 2012/0329122 A1 | 12/2012 | Lipkens | |
| 2013/0061518 A1 | 3/2013 | Schafran | |
| 2013/0079236 A1 | 3/2013 | Holmes | |
| 2013/0116459 A1 | 5/2013 | Marrone | |
| 2013/0137154 A1 * | 5/2013 | Reep | 435/168 |
| 2013/0164798 A1 * | 6/2013 | Vanhercke et al. | 435/134 |
| 2013/0164812 A1 | 6/2013 | Nicholas | |
| 2013/0192130 A1 | 8/2013 | Eckelberry | |
| 2013/0211113 A1 | 8/2013 | Eckelberry | |
| 2013/0228464 A1 | 9/2013 | Eckelberry | |
| 2013/0288329 A1 | 10/2013 | Sanchez | |
| 2014/0017754 A1 | 1/2014 | KALE | |
| 2014/0017755 A1 | 1/2014 | KNIEP | |
| 2014/0017757 A1 | 1/2014 | KNIEP | |
| 2014/0017758 A1 | 1/2014 | KNIEP | |
| 2014/0017759 A1 | 1/2014 | KNIEP | |
| 2014/0017760 A1 | 1/2014 | KNIEP | |

FOREIGN PATENT DOCUMENTS

| | | |
|---|---|---|
| WO | 2010067340 A1 | 6/2010 |
| WO | 2011000079 A1 | 1/2011 |
| WO | 2011054081 A1 | 5/2011 |
| WO | 2011063512 A1 | 6/2011 |
| WO | 2012000056 A1 | 1/2012 |
| WO | 2012054404 A2 | 4/2012 |
| WO | 2013055819 | 4/2013 |
| WO | 2013116357 | 8/2013 |
| WO | 2013158795 | 10/2013 |
| WO | 2014011869 | 1/2014 |

OTHER PUBLICATIONS

Schwartz, David, The AIM Interview: LANL's Jose Olivares, AlgaeIndustryMagazine.com, Jul. 28, 2010, http://www.algaeindustrymagazine.com/aim-interview-lanls-jose-olivares/, accessed Jul. 23, 2012.

Bosma et al., Ultrasound, a new separation technique to harvest microalgae, Journal of Applied Phycology, 2003, pp. 143-153, vol. 15, Kluwer Academic Publishers, Netherlands.

Brennan et al, Biofuels from microalgae—A review of technologies for production, processing, and extractions of biofuels and co-products, Renewable and Sustainable Energy Reviews, 2010, pp. 557-577, vol. 14, Elsevier Ltd.

Coltwell Industries Inc., Telescoping tubing, http://www.coltwell.com/telescoping_tubing.html, accessed Oct. 1, 2012.

Moresco, Justin, Acoustic Algae? Solix & Los Alamos Lab Team Up, Cleantech News and Analysis, Sep. 11, 2009, http://gigaom.com/cleantech/acoustic-algae-solix-los-alamos-lab-team-up/, accessed Jul. 23, 2012.

Loveless, Kolin J., Utilizing standing ultrasonic waves to harvest microalgae from a fluid suspension, Office of Undergraduate Research Texax A&M University, Apr. 2010.

Mide, Volture Piezoelectric energy harvesters, Jun. 3, 2010, Revision No. 001, accessed Aug. 1, 2012.

(56) References Cited

OTHER PUBLICATIONS

Sherrit, Stewart, The Physical Acoustics of Energy Harvesting, IEEE International Ultrasonics Symposium Proceedings, 2008, pp. 1046-1055, Digital Object Identifier 10.1109/ULTSYM.2008.0253.

Sousa, Joe, Gridless tube from 1938, Radiomuseum.org, Jan. 18, 2011, http://www.radiomueseum.org/forum/gridless_tube.html, accessed Oct. 1, 2012.

Originoil, Inc., Algae Appliance, 2011, http://www.originoil.com/pdf/Algae-Appliance-Product-Data-Sheet.pdf., accessed Nov. 29, 2011.

Uduman et al., Dewatering of microalgal cultures: A major bottleneck to algae-based fuels, Journal of Renewable and Sustainable Energy, 2010, pp. 102701-1 to 012701-15, vol. 2, Issue 1, American Institute of Physics.

Originoil, Inc., Company Presentation, 2012. http://www.originoil.com/pdf/OriginOil_Company_Presentation.pdf, accessed Apr. 11, 2012.

Poelman, et al. Potential of electrolytic flocculation for recovery of micro-algae, Resources Conservation and Recycling, 1997, pp. 1-10, vol. 19, Elsevier Science B.V.

Azarian et al., Algae Removal by Electro-coagulation Process, Application for Treatment of the Effluent from an Industrial Wastewater Treatment Plant, Iranian J Publ Health, 2007, pp. 57-64, vol. 36 No. 4, http://journals.tums.ac.ir/.

Gao et al., Electro-coagulation-flotation process for algae removal, Journal of Hazardous Materials, 2010, pp. 336-343, vol. 177, Elsevier B.V., available online Dec. 29, 2009.

Kim et al., Continuous microalgae recovery using electrolysis with polarity exchange, Bioresource Technology, 2012, pp. 268-275, vol. 111, Elsevier Ltd., available online Jan. 28, 2012.

Vandamme et al., Evaluation of Electro-Coagulation-Flocculation for Harvesting Marine and Freshwater Microalgae, Biotechnology and Bioengineering, Oct. 2011, pp. 2320-2329, vol. 108 No. 10, Wiley Periodicals, available online May 6, 2011.

Uduman et al., Electrocoagulation of marine microalgae, Chemeca 2011: Engineering a Better World: Sydney Hilton Hotel, NSW, Australia, Sep. 18-21, 2011. Barton, A.C.T.: Engineers Australia, 2011: [1554]-[1564], http://www.conference.net.au/chemeca2011/papers/420.pdf, accessed Apr. 12, 2012.

Xu et al., Development of an efficient electroflocculation technology integrated with disperse-air flotation for harvesting microalgae, J Chem Technol Biotechnol, 2010; pp. 1504-1507, vol. 85, Society of Chemical Industry, published online by Wiley Online Library Jun. 25, 2010.

Uduman et al., A parametric study of electrocoagulation as a recovery process of marine microalgae for biodiesel production, Chemical Engineering Journal, 2011, pp. 249-257, vol. 174, Elsevier B.V.

Alfafara et al., Operating and scale-up factors for electrolytic removal of algae from eutrophied lakewater, Journal of Chemical Technology and Biotechnology, 2002, pp. 871-876, vol. 77.

Khosla et al., Pulsed electrogeneration of bubbles for electroflotation, Journal of Applied Electrochemistry, 1991, pp. 986-990, vol. 21.

Miao et al., Biodiesel production from heterotrophic microalgal oil, Bioresources Technology, 2006, pp. 841-846, vol. 97.

Yang et al., Chapter 2: Generation of Plasma in Liquid, Plasma Discharge in Liquid, 2012, pp. 15-31, CRC Press, New York, [online] [retrieved Nov. 14, 2012], Retreived from the internet:<URL:http://www.crcnetbase.com/doi/abs/10.1201/b11650-3>.

Mankowski et al., A review of short pulse generator technology, IEEE Transactions on Plasma Science, 2000, pp. 102-108, vol. 28 No. 1.

Austin, "A Shocking Ethanol Enhancer," Ethanol Producer Magazine, Mar. 2009, available at http://www.ethanolproducer.com/article-print.jsp7article id=5355, last visited Apr. 7, 2009, 3 pages.

Friedrich et al., "High Efficiency Electrotransfection with Aluminum Electrodes Using Microsecond Controlled Pulses," Bioelectrochemistry and Bioenergetics, vol. 47, 1998, pp. 103-111.

Li et al, "The Effects of Pulsed Streamerlike Discharge of Cyanobacteria Cells," IEEE Transactions on Plasma Science, Oct. 2006, vol. 34, No. 5, pp. 1719-1724.

Salim, "Biofuels from Microalgae. Harvesting of Algae for Oil Extraction," Thesis, Wageningen University; available at http://www.bpe.wur.nl/wever.internet/Print/vrije content contat./asp, last visited May 20, 2009, 2 pages.

Schultheiss et al., "Processing of Sugar Beets with Pulsed-Electric Fields," IEEE Transactions on Plasma Science, Aug. 2002, vol. 30, No. 4, pp. 1547-1551.

Shimizu, N et al., "A Novel Method of Hydrogen Generation by Water Electrolysis Using an Ultra-short-pulse Power Supply," Journal of Applied Electrochemistry, 2006, 36, pp. 419-423.

Sommerfeld et al., "Application of Electroporation for Lipid Extraction from Microalgae," ASU No date available, 1 pages.

Communication Relating to the Results of the Partial International Search for International Application No. PCT/US2013/050064 as performed by the International Searching Authority, the European Patent Office, mailing date Feb. 3, 2014, 2 pages.

Dufreche et al., "Extraction of Lipids from Municipal Wastewater Plant Microorganisms for Production of Biodiesel," J. Amer. Oil Chem. Soc., 2007, 84, pp. 181-187.

\* cited by examiner

ELECTRICAL MICROORGANISM AGGREGATION METHODS

CROSS-REFERENCE TO RELATED APPLICATIONS

This application claims priority to and is a continuation-in-part of U.S. Ser. No. 13/733,217, filed Jan. 3, 2013 and entitled "Systems, Methods and Apparatuses For Aggregating And Harvesting Microorganisms From An Aqueous Suspension," the entire contents of which, including the claims, are incorporated herein by reference. This application claims priority under 35 U.S.C. §119(e) to U.S. Provisional Application No. 61/707,249, filed Sep. 28, 2012 and entitled "Systems, Methods and Apparatuses For Aggregating And Harvesting Microorganisms From An Aqueous Suspension," the entire contents of which are incorporated herein by reference. This application claims priority under 35 U.S.C. §119(e) to U.S. Provisional Application No. 61/670,888, filed Jul. 12, 2012, and entitled "Systems, Methods and Apparatuses For Aggregating And Harvesting Microorganisms From An Aqueous Suspension," the entire contents of which are incorporated herein by reference.

BACKGROUND

The viability and promise of microorganisms, such as but not limited to algae, microalgae, and cyanobacteria, as a source of intracellular products, such as but not limited to lipids, pigments, and proteins, depends on the ability to: 1) efficiently separate the microorganisms from a liquid suspension, and 2) efficiently extract the intracellular products from the microorganism. If the microorganisms can be efficiently separated from the liquid suspension for extraction, the intracellular products can be used in a variety of products including food, feed, fuel, pharmaceuticals, cosmetics, industrial products, synthesized oil, and fertilizers. Extracting intracellular products from microorganisms in an aqueous suspension is inefficient because of the low density of organisms and complications from the high amounts of water and other constituents of the aqueous suspension. Aggregating the microorganisms and separating the aggregation of organisms from the aqueous suspensions allows for a more efficient extraction process. Current methods of aggregating microorganisms in an aqueous suspension include using chemicals which provide complications in the extraction process, and extended periods of time to dry microorganisms or evaporate the water from the aqueous suspension. Such drying or evaporation techniques inhibit the overall speed of the process. Therefore there is a need for a simple and efficient method of aggregating and separating microorganisms from an aqueous suspension.

SUMMARY OF THE INVENTION

According to various embodiments, the systems, methods and apparatuses of this disclosure generally involve subjecting particles such as microorganisms, particularly algae, microalgae and cyanobacteria, in an aqueous suspension to an electrical current creating an electrical field, electromagnetic field, or acoustic energy field. In some embodiments, the electrical current may be supplied in a constant or continuous manner, such as by direct current. In some embodiments, the electrical current may be a pulsed electrical current and vary sinusoidally, such as in an alternating current. The application of an electrical field causes a change in the surface charge of the microorganisms, which induces the aggregation of the microorganisms into a larger mass through coagulation or flocculation. The application of acoustic energy causes the microorganisms to concentrate at locations of minimum pressure. These methods of aggregation are achieved without disrupting and/or lysing the cell wall or cell membrane of the microorganisms. The aggregated, larger mass is then separated from the aqueous suspension for further processing, such as, but not limited to, an extraction process.

According to some embodiments, the aggregation is achieved by flowing an aqueous suspension containing microorganisms through a channel while simultaneously applying the electrical current as mentioned above. According to various embodiments, the electrical field intensity, electrical field cross-section, flow rate, and channel dimensions are selected in combination with the particular composition of the aqueous suspension to aggregate the microorganisms without lysing or otherwise disrupting the cells of the microorganisms. After aggregation, a portion of the water can be removed from the aqueous suspension by methods such as, but not limited to, decanting and skimming, to produce a concentrated microorganism slurry, which can then be used as input for an extraction process.

According to some embodiments, aggregation using electrical fields facilitates subsequent extraction processes by producing a more concentrated microorganism slurry and reducing the amount of the liquid culture medium in the extraction process. In some embodiments, the concentration of the slurry can be greater than 1% solids while in other embodiments the concentration is greater than 3% or greater than 5%, or in a range from 1% to 30% solids by weight.

In some embodiments, the present invention relates to a system that includes a first apparatus configured to perform aggregation with an electric field to produce an aggregated slurry as discussed above. In some embodiments, the aggregated slurry is in fluid communication with a separation apparatus for separating water from the aggregated microorganisms to produce a concentrated microorganism slurry. In the separation apparatus the aggregated microorganisms may continue to aggregate with other microorganisms in the aqueous suspension to form a larger aggregated mass. The aggregated mass of microorganisms may sink to the bottom of the separation apparatus or float to the surface of the liquid medium in the separation apparatus to facilitate recovery and separation of the aggregated mass of microorganisms. In various embodiments, the aggregated microorganisms exiting the electrical field may be further aggregated by subjecting the microorganisms to multiple passes in the electrical field or a new electrical field.

According to some embodiments of either the systems and/or the methods described previously, regulation of the electrical energy applied to the microorganism(s), such as algae cells, can be controlled by adjusting at least one of the voltage, current, electrical field cross sectional area, pulsation frequency, residence time, flow rate, flow path channel dimensions, and combinations thereof, so that the microorganism(s) is/are subjected to the electrical field in a manner sufficient to achieve the desired effect of aggregating the microorganisms. In this way, according to such embodiments, the microorganisms can be efficiently harvested and dewatered with an efficient use of external energy, which can be accurately controlled and adjusted to create the desired effect or degree of aggregation and/or harvesting. In some additional embodiments, control can be affected manually. In other embodiments, however, the control can be affected automatically with the aid of a computerized sensor and control system. Suitable sensors can be used to measure the rate and/or amount of aggregation and provide output signals to the computer to control the variables of voltage, current, electrical field cross sectional area, pulsation frequency, residence time, flow rate, and flow path channel dimensions that the microorganisms are subjected to. Such sensors may comprise, but are not limited to, turbidity, density, flow rate, chlorophyll a, optical density, electrical current, and electrical voltage sensors. In one non-limiting example turbidity or density sensors can measure the slurry before entering the electrical field and exiting the electrical field to determine and the amount of the aqueous suspension to be separated for further aggregation in a separate apparatus, recycled to the same apparatus for further aggregation, or separated to flow to the other processing paths, such as to the separation apparatus.

According to various embodiments, electrical input frequency rates are determined by biomass density of the microorganisms with pulse rate frequencies being generally increased/decreased proportionally with an increase/decrease in biomass density. In some embodiments, biomass density is determined by using a formula or algorithm comprising a percentage of grams of biomass present per liter of flowing liquid medium. The formula or algorithm can be utilized in the computer based sensor and control system to determine the desired operating parameters by matching the formula or algorithm value to corresponding, operating parameters residing in a matrix of operating parameters and measured effects.

In some embodiments, a separation apparatus is in fluid communication downstream of the aggregating apparatus applying an electrical field, such that the aqueous suspension can flow through electrical field into the separation apparatus. In some embodiments, the separation apparatus applies acoustic energy to the aqueous suspension. In some embodiments, the separation apparatus comprises a foam fractionation device configured to mix the aqueous suspension containing aggregated microorganisms with an injected gas to produce a gas and liquid mixture, and collect a foam comprising aggregated microorganisms. In some embodiments, the separation apparatus is a separation tank. According to at least one embodiment, an element is disposed in the separation tank for producing bubbles or microbubbles. In some embodiments, an aqueous suspension containing aggregated microorganisms is disposed in the flow path of the microbubbles and optionally a pump is disposed in the separation tank for circulating the aqueous suspension. In yet further embodiments, the method further includes the steps of (1) applying a sufficient amount of an electrical current to the aqueous suspension for aggregating the microorganisms, (2) flowing the aqueous suspension containing the electrically treated microorganisms to the separation tank, (3) activating the pump and the element for producing microbubbles resulting in a plurality of microbubbles that impinge upon the aggregated microorganisms so as to cause such microorganisms to float upwards in the aqueous suspension, and (4) separating the floating aggregated microorganisms from the aqueous suspension. In various embodiments, the element disposed in the separation tank for producing microbubbles can be any suitable device or apparatus, e.g. a mixer, a fluidic oscillator, a bubble generator or a microbubble generator.

One aspect of this disclosure provides an apparatus for aggregating microorganisms in an aqueous suspension. The apparatus comprises at least one cathode disposed opposite at least one anode, and at least one pair of spaced insulators disposed between the at least one cathode and the at least one anode. The apparatus also comprises a channel defined between the at least one cathode, at least one anode, and the at least one pair of spaced insulators. The channel has a length commensurate with the lengths of the at least one cathode and at least one anode. The channel defines a fluid flow path for the aqueous suspension to flow through. The channel comprises a cross-section comprising a height and width. At least one of the height and the width of the cross-section of the channel varies over a length of the channel. The apparatus also comprises an electrical power source that is operably connected to the at least one cathode and the at least one anode. When an electric current is applied from the electrical power source to the at least one cathode and the at least one anode, an electrical field is created. The apparatus also comprises a separation tank that is in fluid communication downstream with the channel. The separation tank is configured to collect fluid flow from the fluid flow path defined by the channel.

In some embodiments, at least one of the height and width of the cross-section of the channel increases over the length of the fluid flow path. In some embodiments, at least one of the height and the width decreases of the cross-section of the channel decreases over the length of the fluid flow path.

In some embodiments, the length of the channel may expand or contract. In some embodiments, the apparatus comprises a series of channels of different cross-section size defined by cathodes, anodes, and pairs of insulators, wherein the channels are coupled together in a telescoping configuration. In some embodiments, the cathode, anode, and pair of insulators are disposed within a housing.

In some embodiments, the electrical power source provides continuous electrical current. In some embodiments, the electrical power source provides pulsed electrical current. In some embodiments, the intensity of the electrical current may be changed.

Another aspect of this disclosure is directed to an apparatus for aggregating microorganisms in an aqueous suspension comprising a first electrical conductor disposed within a second electrical conductor, wherein a channel is defined between an exterior surface of the first electrical conductor and an interior surface of the second electrical conductor. The channel defines a fluid flow path for the aqueous suspension. The channel comprises a cross-section comprising a diameter and that diameter varies over a length of the fluid flow path. The apparatus also comprises an electrical power source operably connected to the first electrical conductor and the second electrical conductor. The first electrical conductor is configured as either an anode or a cathode. The second electrical conductor is configured as either an anode or a cathode and is not the same as the first electrical conductor (e.g., if the first electrical conductor is configured as an anode, then the second electrical conductor is configured as a cathode; if the first electrical conductor is configured as a cathode, then the second electrical conductor is configured as an anode). When an electrical current is applied from the electrical power source to the first electrical conductor and the second electrical conductor, an electrical field is created. The apparatus also comprises a separation tank in fluid communication downstream with the channel. The separation tank is configured to collect fluid flow from the fluid flow path defined by the channel.

In some embodiments, the diameter of the cross-section increases over a length of the channel. In some embodiments, the diameter of the cross-section decreases over a length of the channel.

In some embodiments, the length of the channel may expand or contract.

In some embodiments, the apparatus comprises a series of channels of different cross-section size defined by first and second electrical conductors and pairs of insulators, wherein the channels are coupled together in a telescoping configuration. In some embodiments, the first electrical conductor, the second electrical conductor, and pair of insulators are disposed within a housing.

In some embodiments, the electrical power source provides continuous electrical current. In some embodiments, the electrical power source provides pulsed electrical current.

Another aspect of this disclosure is directed to a method for aggregating microorganisms in an aqueous suspension. In the method, an aqueous suspension comprising microorganisms is flowed into at least one apparatus. The apparatus comprises at least one cathode disposed opposite at least one anode, and at least one pair of spaced insulators disposed between the at least one cathode and the at least one anode. The apparatus also comprises a channel defined between the at least one cathode, at least one anode, and the at least one pair of spaced insulators. The channel has a length commensurate with the lengths of the at least one cathode and at least one anode. The channel defines a fluid flow path for the aqueous suspension to flow through. The channel comprises a cross-section comprising at least one of a height, width, and diameter. At least one of the height, width, and diameter of the cross-section of the channel varies over at least a portion of the length of the fluid flow path. The apparatus also comprises an electrical power source that is operably connected to the at least one cathode and the at least one anode. When an electric current is applied from the electrical power source to the at least one cathode and the at least one anode, an electrical field is created. The apparatus also comprises a separation tank that is in fluid communication downstream with the channel. The separation tank is configured to collect fluid flow from the fluid flow path defined by the channel. In the method, after flowing the aqueous suspension comprising microorganisms into at least one apparatus, the aqueous suspension is then flowed through the channel and into the separation tank. An electrical current is applied from the electrical power source to the at least one cathode and the at least one anode, thereby creating an electrical field in the channel, wherein the surface charge of the microorganisms in the aqueous suspension in the fluid flow path is treated, and wherein the microorganisms aggregate with similarly treated microorganisms in the aqueous suspension without disrupting the cell membranes of the microorganisms. The microorganisms are aggregated in the separation tank. Then, the aggregated microorganisms are separated from the aqueous suspension in the separation tank.

In some embodiments, the at least one apparatus used in the method comprises a plurality of apparatuses in parallel configuration. In some embodiments, the at least on apparatus comprises a plurality of apparatuses in a series configuration. In some embodiments, the at least on apparatus comprises a plurality of apparatuses in a combination of parallel and series configurations.

In some embodiments, the electrical power source provides continuous electrical current. In some embodiments, the electrical power source provides pulsed electrical current.

Another aspect of this disclosure is directed to a system for aggregating microorganisms in an aqueous suspension comprising a plurality of aggregating apparatuses. Each aggregating apparatus comprises at least one electrical conductor comprising a conductive material configured as a cathode and at least one electrical conductor comprising conductive material configured as an anode. The electrical conductor comprising a conductive material configured as a cathode is disposed opposite the at least one electrical conductor comprising conductive material configured as an anode. Each apparatus also comprises at least one pair of spaced insulators disposed between the at least one electrical conductor comprising a conductive material configured as a cathode and the at least one electrical conductor comprising a conductive material configured as an anode. Each apparatus also comprises a channel defined between the at least one electrical conductor comprising a conductive material configured as a cathode, at least one electrical conductor comprising a conductive material configured as an anode, and the at least one pair of spaced insulators. The channel has a length commensurate with the lengths of the at least one electrical conductor comprising a conductive material configured as a cathode and the at least one electrical conductor comprising a conductive material configured as an anode. The channel defines a fluid flow path for the aqueous suspension to flow through. The channel comprises a cross-section comprising at least one of a height, width, and diameter. At least one of the height, width, and diameter of the cross-section of the channel varies over at least a portion of the length of the fluid flow path. The apparatus also comprises an electrical power source that is operably connected to the at least one electrical conductor comprising a conductive material configured as a cathode and the at least one electrical conductor comprising a conductive material configured as an anode. When an electric current is applied from the electrical power source to the at least one electrical conductor comprising a conductive material configured as a cathode and the at least one electrical conductor comprising a conductive material configured as an anode, an electrical field is created. In this system, at least one of the aggregating apparatuses differs from at least one other aggregating apparatus by at least one characteristic selected from the group consisting of the conductive material of the at least one electrical conductor comprising a conductive material configured as a cathode, the conductive material of the at least one electrical conductor comprising a conductive material configured as an anode, the intensity of the electrical field, the fluid flow path height, the fluid flow path width, the fluid flow path diameter, and the length of the channel.

In some embodiments, the conductive material is selected from the group consisting of aluminum, copper, titanium, nickel, steel, stainless steel, graphite, and a conductive polymer. In some embodiments, the conductive material comprises a coating of at least one of iridium, ruthenium, platinum, rhodium, tantalum, and a mixed metal polymer.

In some embodiments, the system comprises a plurality of aggregating apparatuses configured in parallel. In some embodiments, the system comprises a plurality of aggregating apparatuses configured in series. In some embodiments, the system comprises a plurality of aggregating apparatuses configured in a combination of parallel and series configurations.

In some embodiments, the electrical power source provides continuous electrical current. In some embodiments, the electrical power source provides pulsed electrical current. In some embodiments, at least one of the aggregating apparatuses differs from at least one other aggregating apparatus by electrical pulse type.

Another aspect of this disclosure is directed to a method for aggregating microorganisms in an aqueous suspension, the method comprising flowing an aqueous suspension comprising microorganisms into an aggregating apparatus or a plurality of aggregating apparatuses. Each aggregating apparatus comprises at least one electrical conductor comprising a conductive material configured as a cathode and at least one electrical conductor comprising conductive material configured as an anode. The electrical conductor comprising a conductive material configured as a cathode is disposed opposite the at least one electrical conductor comprising conductive material configured as an anode. Each apparatus also comprises at least one pair of spaced insulators disposed between the at least one electrical conductor comprising a conductive material configured as a cathode and the at least one electrical conductor comprising a conductive material configured as an anode. Each apparatus also comprises a channel defined between the at least one electrical conductor comprising a conductive material configured as a cathode, at least one electrical conductor comprising a conductive material configured as an anode, and the at least one pair of spaced insulators. The channel has a length commensurate with the lengths of the at least one electrical conductor comprising a conductive material configured as a cathode and the at least one electrical conductor comprising a conductive material configured as an anode. The channel defines a fluid flow path for the aqueous suspension to flow through. The channel comprises a cross-section comprising at least one of a height, width, and diameter. At least one of the height, width, and diameter of the cross-section of the channel varies over at least a portion of the length of the fluid flow path. The apparatus also comprises an electrical power source that is operably connected to the at least one electrical conductor comprising a conductive material configured as a cathode and the at least one electrical conductor comprising a conductive material configured as an anode. When an electric current is applied from the electrical power source to the at least one electrical conductor comprising a conductive material configured as a cathode and the at least one electrical conductor comprising a conductive material configured as an anode, an electrical field is created. In this system, at least one of the aggregating apparatuses differs from at least one other aggregating apparatus by at least one characteristic selected from the group consisting of the conductive material of the at least one electrical conductor comprising a conductive material configured as a cathode, the conductive material of the at least one electrical conductor comprising a conductive material configured as an anode, the intensity of the electrical field, the fluid flow path height, the fluid flow path width, the fluid flow path diameter, and the length of the channel. In the method, the aqueous suspension comprising microorganisms flows through the channel into a separation tank. An electrical current is applied from the electrical power source to the at least one electrical conductor comprising a conductive material configured as a cathode and the at least one electrical conductor comprising a conductive material configured as an anode, wherein an electrical field comprising an intensity is created, wherein the electrical field treats the surface charges of the microorganisms and causes similarly treated microorganisms to aggregate in the aqueous suspension without disrupting the cell membranes. Next, the microorganisms are aggregated in the separation tank. Then, the aggregated microorganisms are separated from the aqueous suspension in the separation tank.

In some embodiments, the conductive material is selected from the group consisting of aluminum, copper, titanium, nickel, steel, stainless steel, graphite, and a conductive polymer. In some embodiments, the conductive material comprises a coating of at least one of iridium, ruthenium, platinum, rhodium, tantalum, and a mixed metal polymer.

In some embodiments, the system comprises a plurality of aggregating apparatuses configured in parallel. In some embodiments, the system comprises a plurality of aggregating apparatuses configured in series. In some embodiments, the system comprises a plurality of aggregating apparatuses configured in a combination of parallel and series configurations.

In some embodiments, the electrical power source provides continuous electrical current. In some embodiments, the electrical power source provides pulsed electrical current.

In some embodiments, at least one of the aggregating apparatuses differs from at least one other aggregating apparatus by electrical pulse type.

In some embodiments, the aggregating apparatus further comprises a separation tank in fluid communication downstream from the channel. The separation tank can be configured to collect fluid flow from the fluid flow path defined by the channel.

In some embodiments, at least a portion of the aqueous suspension exiting the fluid flow path of the apparatus is recirculated back through the apparatus.

In some embodiments, the method further comprises measuring with a sensor at least one of the density and turbidity of the aqueous suspension and transmitting the measurement value to a computer controller. In some embodiments, the computer controller receives the measurement value from the sensor and, based on that measurement value, can adjust the volume of the portion of the aqueous suspension that is recirculated through the apparatus. In some embodiments, the portion of aqueous suspension that is recirculated is mixed with an untreated volume of aqueous suspension comprising microorganisms in a continuous aggregation process. In further embodiments, the aqueous suspension exiting the apparatus is recirculated to the apparatus until the measurement value reaches a threshold value in a batch aggregation process.

Another aspect of this disclosure is directed to an apparatus for aggregating microorganisms in an aqueous suspension. The apparatus comprises a vessel configured to contain an aqueous suspension of microorganisms and configured for fluid communication with a housing. The apparatus also comprises at least one first electrical conductor configured as a cathode disposed within the housing, at least one second electrical conductor configured as an anode disposed within the housing, at least one third electrical conductor configured as a collector electrode disposed within the housing and adjacent to the at least one first electrical conductor, at least one fourth electrical conductor configured as a control electrode disposed within the housing and adjacent to the at least one first electrical conductor, wherein the at least one first electrical conductor is at least partially surrounded by the at least one second electrical conductor such that a channel is defined between an exterior surface of the at least one first electrical conductor and an interior surface of the at least one second electrical conductor, providing a fluid flow path configured for receiving the aqueous suspension from the vessel. The apparatus also comprises at least one electrical power source operably connected to the at least one first electrical conductor, second electrical conductor, third electrical conductor, and fourth electrical conductor, wherein an electrical field is created by providing an electrical current from the electrical power source to the at least one first electrical conductor, second electrical conductor, third electrical conductor, and fourth electrical conductor wherein a cross-sectional area of the electrical field is adjustable based on the current applied to the at least one third electrical conductor and the at least one fourth electrical conductor.

In further embodiments, the apparatus further comprises a separation tank configured to receive the aqueous suspension exiting the fluid flow path.

In some embodiments, the at least one first electrical conductor has a circular cross-section or a polygonal cross-section. In some embodiments, the at least one second electrical conductor has a curved semi-circular cross-section or a circular cross-section. In some embodiments, the at least one third electrical conductor has a circular cross-section, a polygonal cross-section, a v-shaped cross section, an oval cross-section or a curved cross section. In some embodiments, the at least one fourth electrical conductor has a circular cross-section, oval cross-section or a polygonal cross-section.

In other embodiments, the at least one third electrical conductor and the at least one second electrical conductor have a positive potential relative to the at least one first electrical conductor, the at least one second electrical conductor has a larger positive potential than the at least one third electrical conductor, and the at least one fourth electrical conductor has a negative potential relative to the at least one first electrical conductor.

In some embodiments, the cross-sectional area of the electrical field is adjusted by increasing or decreasing the negative potential of the at least one third electrical conductor. In other embodiments, the cross-sectional area of the electrical field is adjusted by increasing or decreasing the negative potential of the at least one fourth electrical conductor. In some embodiments, the cross-sectional area of the electrical field is adjusted by increasing or decreasing the negative potential of the at least one third electrical conductor and at least one fourth electrical conductor.

In some embodiments, the electrical power source provides continuous electrical current. In some embodiments, the electrical power source provides pulsed electrical current.

Another aspect of this disclosure is directed to a method for aggregating microorganisms in an aqueous suspension. The method comprises flowing an aqueous suspensions comprising microorganisms into an apparatus. The apparatus comprises at least one electrical conductor with a first potential, at least one second electrical conductor with a second potential, at least one third electrical conductor with a third potential, and at least one fourth electrical conductor with a fourth potential, the at least one first electrical conductor being disposed such that a channel is defined between the at least one first electrical conductor and the at least one second electrical conductor, wherein the channel defines a fluid flow path for the aqueous suspension. The apparatus also comprises at least one electrical power source operably connected to the at least one first electrical conductor, second electrical conductor, third electrical conductor, and fourth electrical conductor, wherein an electrical field is created by providing an electrical current from the electrical power source to the at least one first electrical conductor, second electrical conductor, third electrical conductor, and fourth electrical conductor. Next, the method comprises applying an electrical current to the at least one first electrical conductor, second electrical conductor, third electrical conductor, fourth electrical, and aqueous suspension whereby the surface charge of the microorganisms is treated and the microorganisms aggregate with similarly treated microorganisms in the aqueous suspension without disrupting the cell membrane. The method also comprises adjusting the at least one power source to change the potential of at least one of the third electrical conductor and fourth electrical conductor, wherein the change in potential of the at least one third electrical conductor or fourth electrical conductor changes the cross-sectional area of the electrical field.

In some embodiments, the at least one third electrical conductor and the at least one second electrical conductor have a positive potential relative to the at least one first electrical conductor, the at least one second electrical conductor has a larger positive potential than the at least one third electrical conductor, and the at least one fourth electrical conductor has a negative potential relative to the at least one first electrical conductor. In some embodiments, the electrical power source provides continuous electrical current. In some embodiments, the electrical power source provides pulsed electrical current.

Another aspect of this disclosure is directed to a method of aggregating microorganisms in an aqueous solution. The method comprises providing an aqueous solution feed comprising a liquid and microorganisms dispersed therein and aggregating the aqueous suspension feed. The aggregating comprises applying a pulsed electric field to the aqueous suspension, the pulsed electrical field generated by a power source and a pulse generator, wherein said pulse generator produces a pattern of electrical pulses which vary in a pulse type comprising at least one of a pulse amplitude, a pulse duration, a pulse shape, and a pause duration between pulses.

In some embodiments, the pulse shape is rectangular, trapezoidal, exponentially decaying, unipolar, or bipolar. In some embodiments, the pulse duration ranges from 1 to 1,000 nanoseconds. In some embodiments, the pattern of electrical pulses alternates between two pulse types. In some embodiments, the pattern of electrical pulses comprises more than two pulse types. In other embodiments, the pattern of electrical pulses utilized by the pulse generator comprises a programmed pattern. In further embodiments, the programmed pattern is selected by a computerized controller based on at least one of a measured turbidity of the aqueous solution, a measured density of the aqueous solution, a composition of the aqueous solution, and a flow rate of the aqueous solution.

Yet another aspect of this disclosure is directed to a system for aggregating microorganisms in an aqueous suspension The system comprises at least one apparatus comprising at least one electrode, said at least one electrode in electrical communication with a at least one power supply and in liquid communication with an aqueous solution feed comprising microorganisms and a liquid, the at least one power supply comprising a pulse generator and configured to apply a pattern of electrical pulses which vary in a pulse type comprising at least one of a pulse amplitude, a pulse duration, a pulse shape, and a pause duration between pulses, to the aqueous suspension. The system also comprises a separation tank in fluid communication with the apparatus for receiving the aqueous suspension after application of the pattern of electrical pulses.

In some embodiments, the pulse shape is rectangular, trapezoidal, exponentially decaying, unipolar, or bipolar. In some embodiments, the pulse duration ranges from 1 to 1,000 nanoseconds. In some embodiments, the pattern of electrical pulses alternates between two pulse types. In further embodiments, the pattern of electrical pulses comprises more than two pulse types. In other embodiments, the pattern of electrical pulses utilized by the pulse generator comprises a programmed pattern. In some embodiments, the programmed pattern is selected by a computerized controller based on at least one of a measured turbidity of the aqueous solution, a measured density of the aqueous solution, a composition of the aqueous solution, and a flow rate of the aqueous solution.

Yet another aspect of this disclosure is directed to a system for aggregating microorganisms in an aqueous suspension The system comprises a device configured to apply an electric field to an aqueous suspension. The device comprises at least one first electrical conductor, at least one second electrical conductor, wherein the at least one first electrical conductor is disposed within the at least one second electrical conductor, such that a channel is defined between an exterior surface of the at least one first electrical conductor and an interior surface of the at least one second electrical conductor and with a cross-section comprising a diameter, the channel providing a fluid flow path for the aqueous suspension. The device also comprises an electrical power source operably connected to the at least one first electrical conductor and the at least one second electrical conductor, wherein electrical field is created when an electric current is provided from the electrical power source to the at least one first electrical conductor and the at least one second electrical conductor and the aqueous suspension. The system also comprises a device configured to apply an acoustic wave to the aqueous suspension, the device comprising a tube configured to contain a flow of the aqueous suspension, at least one transducer coupled to the tube, and a generator configured to produce and transmit electrical radio frequency signals, wherein the generator transmits an electrical radio frequency signal to the transducer and the transducer converts the electrical signal into an acoustic signal which vibrates the tube and creates a wave with a pressure minima node at a location within the tube, wherein the device configured to apply an electrical field and the device configured to apply an acoustic wave to the aqueous suspension are in fluid communication, and wherein the device configured to apply an electrical field and the device configured to apply an acoustic wave to the aqueous suspension each use pulsed electrical energy.

In some embodiments, the pressure minima node is located at the central axis of the tube. In other embodiments, the minima node is located at the interior wall of the tube. In further embodiments, the system further comprises a collector disposed in the tube configured to receive and separate a portion of the flow of the aqueous suspension.

In other embodiments, the system further comprises a piezoelectric vibration energy harvester coupled to the tube and configured to convert vibration energy into electrical current. In some embodiments, the wave is a standing wave. In other embodiments, the wave is a traveling wave.

In further embodiments, the device configured to apply an electric field further comprises at least one third and at least one fourth electrical conductors. In other embodiments, a cross-section of the electrical field may be adjusted by tuning the electrical conductors. In still other embodiments, the device is configured to apply an electric field further comprises a cross section of the flow path which varies over a length of the flow path.

Another aspect of this disclosure is directed to a method of aggregating microorganisms in an aqueous medium. The method comprises flowing an aqueous medium comprising microorganisms of a first type through a first tube and a second tube. Next, the method comprises applying pulsed acoustic energy to the first tube to generate a standing wave with a pressure minima node within the first tube. Then the method comprises applying pulsed electrical energy to the second to tube to generate an electrical field within the second tube.

In some embodiments, the aqueous medium flows through the first tube before the second tube, the acoustic energy is applied to the aqueous medium first to selectively target microorganisms of the first type and concentrate the microorganisms of the first type at a pressure minima node, the concentrate of microorganisms of the first type are separated from the aqueous medium by a collector disposed within the first tube, and the electrical energy is applied to the concentrate of microorganisms of the first type to further induce aggregation.

In some embodiments, the aqueous medium flows through the second tube before the first tube, the electrical energy is applied to the aqueous medium first to induce aggregation of the microorganisms of the first type, next apply the acoustic energy to the aqueous medium to further concentrate the microorganisms of the first type, separating the aggregated microorganisms of the first type from the aqueous medium through a collector disposed within the first tube, and recycling the aqueous medium for further electrical energy application.

In some embodiments, an electrical field created by the pulse electrical field may be tuned to adjust a cross section of the electric field. In some embodiments, a flow path of the second tube may change in cross section over a length of the second tube.

Another aspect of this disclosure is directed to an apparatus for aggregating microorganisms in an aqueous suspension. The apparatus comprises a tube configured to contain a flow of an aqueous suspensions comprising microorganisms, an anode disposed within the tube and with a length parallel to a concentric longitudinal axis of the tube, and a cathode disposed within the tube, and with a length parallel to the anode forming a gap between the anode and cathode comprising the concentric longitudinal axis of the tube. The apparatus also comprises an electrical power source operably connected to the anode and the cathode for creating an electrical field by providing an electric current that is applied between the anode and cathode and the aqueous suspension, at least one transducer coupled to the tube, and a generator configured to produce and transmit radio frequency signals. In this apparatus, the generator transmits an electrical radio frequency signal to the transducer and the transducer converts the electrical signal into an acoustic signal which vibrates the tube and creates a standing wave with a pressure minima node at a location between the anode and cathode.

In some embodiments, the electrical field and acoustic standing wave are applied simultaneously to the aqueous suspension. In some embodiments, the apparatus further comprises a piezoelectric vibration energy harvester coupled to the tube and configured to convert vibration energy into electrical current. In some embodiments, the electrical field is pulsed. In other embodiments, the acoustic signal is pulsed.

Another aspect of this disclosure is directed to an apparatus for aggregating microorganisms in an aqueous suspension. The apparatus comprises at least one first electrical conductor configured as a cathode, at least one second electrical conductor configured as an anode, and at least one pair of spaced insulators disposed between the at least one first electrical conductor and the at least one second electrical conductor, the at least one first conductor being disposed opposite the at least one second electrical conductor, such that a channel is defined between the at least one first electrical conductor, the at least one second electrical conductor, and the at least one pair of spaced insulators, the channel providing a fluid flow path for the aqueous suspension. The apparatus also comprises an electrical power source operably connected to the at least one first electrical conductor and the at least one second electrical conductor, wherein an electrical field is created by providing an electric current from the electrical power source to the at least one first electrical conductor and the at least one second electrical conductor. The apparatus also comprises at least one first transducer coupled to the at least one first electrical conductor, at least one second transducer coupled to the at least one second electrical conductor, and a generator configured to produce and transmit electrical radio frequency signals. In the apparatus, the generator transmits an electrical radio frequency signal to the at least one first and second transducers, and the transducers convert the electrical signal into an acoustic signal which vibrates the at least one first electrical conductor and the at least one second electrical conductor, and creates a standing wave with a pressure minima node at a location between the at least one first electrical conductor and the at least one second electrical conductor.

In some embodiments, the electrical field and acoustic standing wave are applied simultaneously to the aqueous suspension. In some embodiments, the apparatus further comprises a piezoelectric vibration energy harvester coupled to the at least one first electrical conductor or the at least one second electrical conductor and configured to convert vibration energy into electrical current. In some embodiments, the electrical field is pulsed. In some embodiments, the acoustic signal is pulsed.

The particles separated by the system of the present invention are usually living organisms or parts of living plant, animal or microbial organisms. Typically microorganisms and single cell or relatively few cells clumps, organelles or whole organisms are separated from a liquid. Microorganisms suitable for the systems, methods and apparatuses described comprise, but are not limited to, algae, microalgae, and cyanobacteria. Non-limiting examples of microalgae that can be used with the methods of the invention are members of one of the following divisions: Chlorophyta, Cyanophyta (Cyanobacteria), and Heterokontophyta. In certain embodiments, the microalgae used with the methods of the invention are members of one of the following classes: Bacillariophyceae, Eustigmatophyceae, and Chrysophyceae. In certain embodiments, the microalgae used with the methods of the invention are members of one of the following genera: *Nannochloropsis, Chlorella, Dunaliella, Scenedesmus, Selenastrum, Oscillatoria, Phormidium, Spirulina, Amphora,* and *Ochromonas*.

Non-limiting examples of microalgae species that can be used with the methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana*.

In some embodiments, the microorganisms are cultured autotrophically or phototrophically. In some embodiments, the microorganisms are cultured mixotrophically. In some embodiments, the microorganisms are cultured heterotrophically.

The concentration of the microorganisms in the aqueous suspension will depend in part on the type of microorganism, size of the microorganism, maturity of the microorganism, cell wall characteristics of the microorganism, contaminant load, the culture temperature, the culture pH, the culture salinity level, available nutrients and other various parameters which may be modified or adjusted according to various embodiments. In other embodiments, such parameters are dictated by nature or the natural environment and the available resources. In some embodiments, the aqueous slurry is cultured and used in the methods and systems at any suitable concentration, such as, but not limited to, a range from about 100 mg/L to about 5 g/L (e.g., about 500 mg/L to about 1 g/L).

According to some embodiments, the pH of the slurry during aggregation can vary. In various embodiments, the pH is alkaline. However, in other embodiments, acid or base can be added to keep the pH at a desired level or measure, which can be kept in a range from 6-10.

DETAILED DESCRIPTION

Rectangular Channel Embodiment

Figure 1:
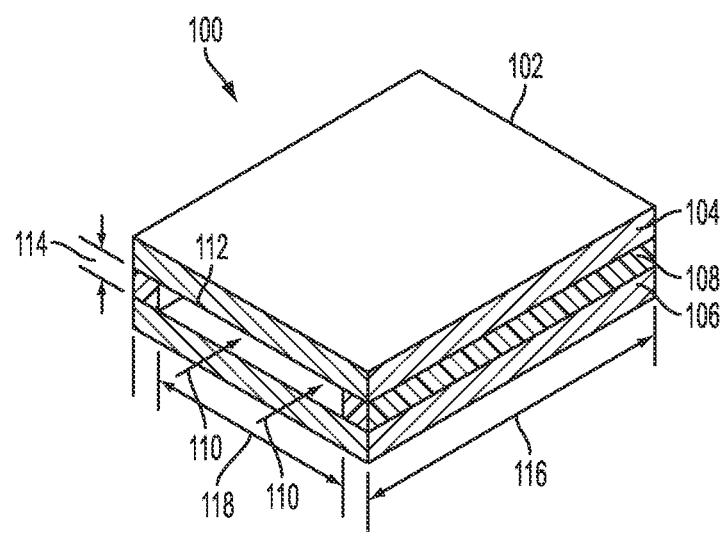
FIG. 1 shows a rectangular channel embodiment of an aggregation device.

With reference to the Figures, the methods, systems and apparatuses described generally will now be discussed in greater detail with reference to illustrative embodiments. According to various embodiments, some methods include providing an aggregation apparatus that includes, among other things, a channel or fluid path for flowing the microorganisms through an electrical field that is sufficiently strong to aggregate the microorganisms without causing lysing or disruption of the microorganism cell walls or membranes. In some further embodiments, the apparatus includes an anode and a cathode that form a channel through which the aqueous slurry can flow. For example, FIG. 1 illustrates a schematic of a portion of an aggregation device 100 that is suitable for use in various methods according to some embodiments. In such embodiments, the illustrated portion of aggregation device 100 includes a body 102 that comprises an anode 104 and a cathode 106 electrically separated by an insulator 108. In various embodiments, anode 104 and cathode 106 are spaced apart to form a channel 112 that defines a fluid flow path 110. According to various embodiments, channel 112 has a length 116 that extends the length of the anode and cathode exposed to the fluid flow path 110. Likewise, in various embodiments, channel 112 also has a width 118 that is defined by the space between the insulators 108 that is exposed to the anode 104 and cathode 106. Thus, as illustrated in FIG. 1, and according to some embodiments, channel 112 is bounded on its sides so as to form an opening and an exit through which fluid can be caused to flow (e.g., by pumping, gravity). In some embodiments, the spaced insulators are not used and instead the anode 104 and cathode 106 are disposed in an opposing arrangement within a housing.

According to some embodiments, as further illustrated in FIG. 1, the gap height 114 between anode 104 and cathode 106 has a distance suitable for applying an electrical field to the aqueous suspension. In at least one embodiment, for example, gap 114 is in a range from 0.5 mm to 200 mm. In various embodiments, gap height 114 is in a range from 1 mm to 50 mm while in other embodiments gap height 114 is in a range from 2 mm to 20 mm. In some embodiments, the narrow gap height 114 coupled with a comparatively large width 118 and length 116 can provide a large volume for channel 112 while maintaining a strong electrical field for aggregating the microorganisms.

In some embodiments, width 118 of channel 112 can be any width so long as the materials of anode 104 and cathode 106 are sufficiently strong to span the width without contacting one another and thus shorting the system or apparatus. In at least one embodiment, the volume of channel 112 between anode 104 and cathode 106 and within gap distance 114, (i.e., the gap volume) is at least 50 ml. In other embodiments, however, the gap volume is at least 200 ml while in other embodiments the gap volume is at least 500 ml. In yet additional embodiments, the gap volume is at least 1 liter. In other embodiments, the gap volume exceeds 1 liter. In additional embodiments, the surface area of anode 104 and cathode 106 exposed to fluid flow 110 (i.e. the gap surface area) is at least 500 cm². In other embodiments, the gap surface area is at least 1000 cm² while in other embodiments the gap surface area is at least 2000 cm². In yet other embodiments, the gap surface area exceeds 2000 cm².

Varying Channel Dimensions Embodiment

Figure 2A:
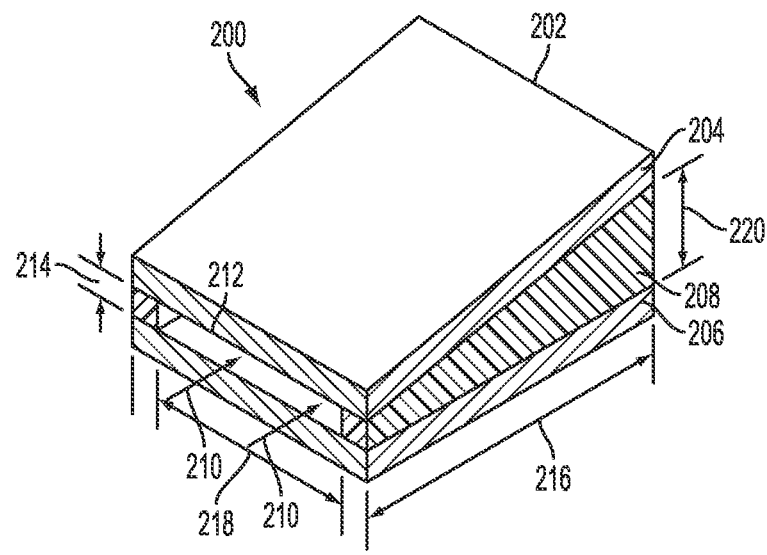
FIG. 2A shows a rectangular channel embodiment of an aggregation device where the height of the channel varies over the length of the channel.
Figure 2B:
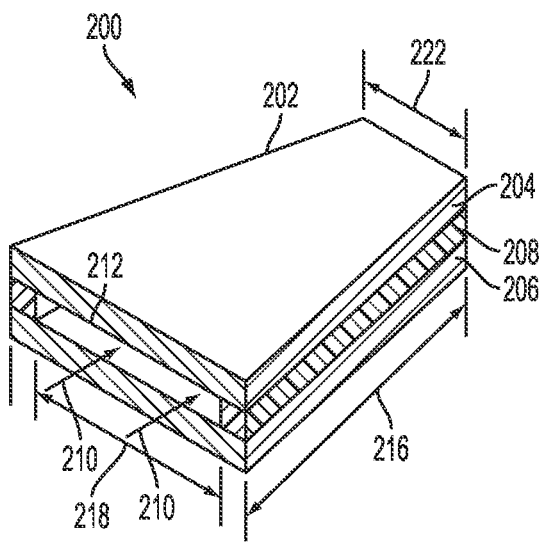
FIG. 2B shows a rectangular channel embodiment of an aggregation device where the width of the channel varies over the length of the channel.

In some embodiments, the gap width 118 and/or the gap height 114 can vary over the length of the channel, as illustrated in FIGS. 2A and 2B. In some embodiments with a long flow path length, long residence time or recirculation of the electrically treated aqueous suspension the microorganisms may aggregate while within the channel flow path. A gap increasing in width and/or height over the length allows for fewer clogs as the microorganisms aggregate over the length of the flow path, and decreases the flow rate exiting the flow path 210. In other embodiments, a gap decreasing in width and/or height over the length creates a nozzle and an increase in the flow rate exiting the flow path 210. The desired flow rate exiting the flow path may depend on the shear sensitivity of aggregations of microorganisms that form within the flow path. In further embodiments, a gap varying in width and/or height over the length with a consistent current supply will adjust the properties of the electrical field over the length of the channel by increasing or decreasing the intensity without adjusting the amount of current used.

In the aggregation device 200, the change in the gap width 118 and/or the gap height 114 over the length of the body 202 can be achieved through various means such as, but not limited to, the shape of the insulators 208, the shape of the anode 204, the shape of the cathode 206, or any combination thereof. In some embodiments, the height 220 of at least one of the insulators 208 increases over the length 216 of the channel 212. For example, as illustrated in FIG. 2A, gap height 220 is greater than gap height 214. Conversely, in some embodiments, although not shown, the height of the insulators 208 decreases over the length 216 of the channel 212 so that gap height 220 is less than gap height 214. In some embodiments, the width 218 of the cathode 206 increases over the length of the channel 212. In some embodiments, the width 218 of the cathode 206 decreases over the length of the channel. For example, as illustrated in FIG. 2B, gap width 222 is smaller than gap width 218. Conversely, in some embodiments, the gap width decreases over the length of the channel. For example, in some embodiments, although not shown, gap width 222 can be greater than gap width 218. In some embodiments, the width of the anode increases over the length of the channel. In some embodiments, the width of the anode decreases over the length of the channel. In some embodiments, the width and height of the channel can both vary over the length of the channel.

Figure 3A:
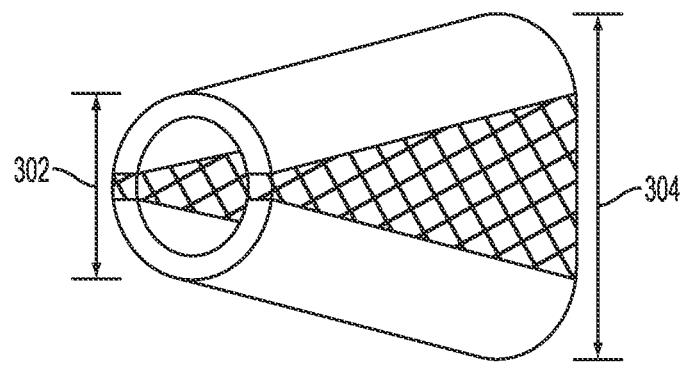
FIG. 3A shows an embodiment with a channel formed by curved semi-circular electrodes separated by a pair of insulated spacers where the diameter of the channel varies over the length of the channel.

In some embodiments, the channel is formed by a curved semi-circular anode and a curved semi-circular cathode separated by a pair of insulators, and has a circular cross-section. The circular cross-section may have a diameter increasing or decreasing over the length of the channel, similar to the height and width described above, to form a conical shaped channel. For example, in some embodiments, as shown in FIG. 3A, diameter 304 can be greater than diameter 302. Conversely, in some embodiments, although not shown, diameter 304 can be less than diameter 302.

Figure 3B:
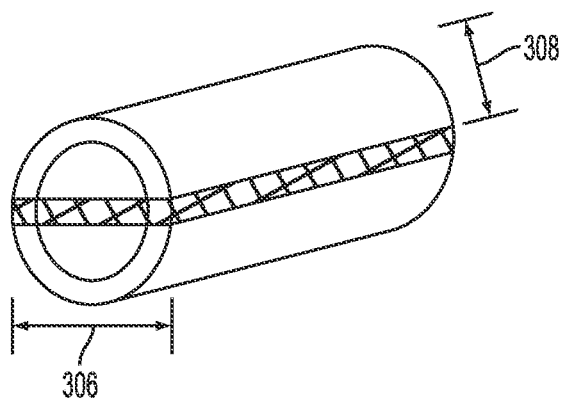
FIG. 3B shows an embodiment with a channel formed by curved electrodes separated by a pair of insulated spacers where the height and width of the channel can vary over the length of the channel.
Figure 4A:
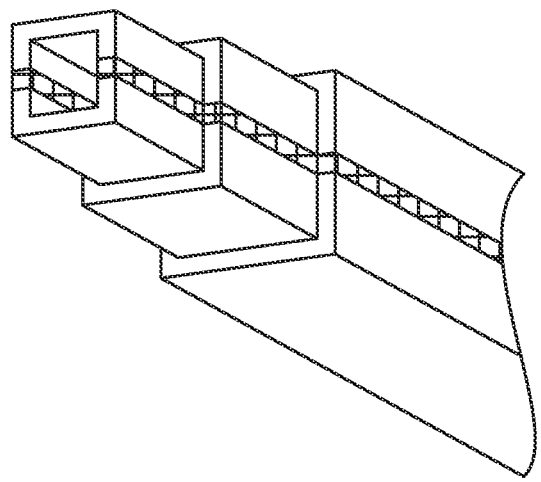
FIG. 4A shows an embodiment with a series of rectangular channels coupled in a telescoping arrangement.
Figure 4B:
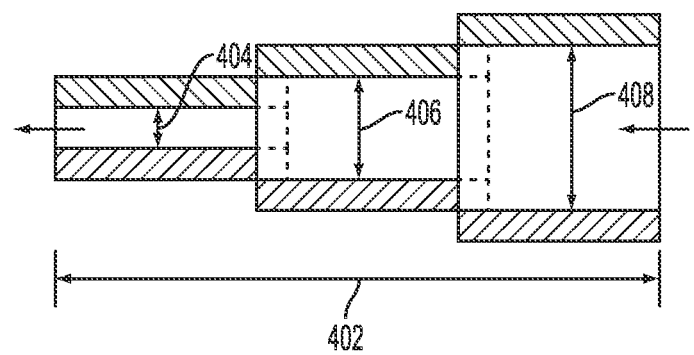
FIG. 4B shows a side view of an embodiment with a series of rectangular channels coupled in a telescoping arrangement.
Figure 4C:
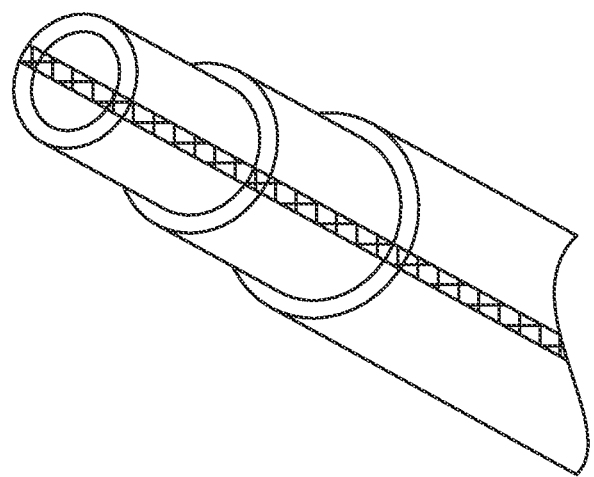
FIG. 4C shows an embodiment with a series of curved channels coupled in a telescoping arrangement.

In other embodiments, the channel is formed by a curved anode and curved cathode separated by a pair of insulator, and has a curved cross-section that has a height and a width. Such an embodiment is illustrated in FIG. 3B, which depicts width 306 and height 308. The height and width may vary over the length of the channel, so that the curved cross-section varies in size and shape over the length of the channel.

According to some embodiments, the length of the channel is the dimension commensurate with or in the direction of fluid flow (the longitudinal direction) and can be any length so long as the channel is not occluded by clogging (e.g., with the microorganism aqueous suspension flowing there through) or hampered by significant pressure drops which decrease the flow rate below a desired value. In at least one embodiment, the length of the channel is at least 25 cm. In other embodiments, however, the length is 50 cm, while in other embodiments the length is 100 cm. In still other embodiments, the length is at least 200 cm, while in yet other embodiments the length exceeds 200 cm. In additional embodiments, the length can be less than 1000 cm, less than 500 cm, or less than 250 cm.

Adjustable Channel Dimensions Embodiment

In some embodiments, the dimensions of the channel are fixed. In other embodiments, the gap width, the gap height of the channel, and the length of the channel are adjustable. An adjustable channel provides another method of adjusting the electric field and flow rate without changing the power source or pumps. An adjustable channel, such as a telescoping configuration, also allows the apparatus to adjust in size to be retro fit into fixed spaces and allows for easier transportation when collapsed.

In some embodiments, the channel comprises a series of channels coupled in a telescoping manner as illustrated in FIG. 4A. In a telescoping arrangement the channel may be uniform when collapsed, and may have a decreasing height and width or an increasing height and width when the length is extended. For example, as shown in FIG. 4B, when a telescoping embodiment is extended over length 402, the height of the series of channels can decrease over length 402 so that height 408 is greater than height 406 which is greater than height 404. The telescoping configuration can also be arranged so that that the algal suspension flows in the opposite direction than as illustrated in FIG. 4B, i.e., so that the height of the series of channels increases over length 402. The nested channels of a telescoping arrangement may be constructed as described above with an anode, cathode, and insulators forming the boundaries of the channel.

In addition to the embodiments having telescoping rectangular channels shown in FIGS. 4A and 4B, other telescoping embodiments have a series of channels formed by curved semi-circular anodes and curved semi-circular cathodes separated by a pair of insulators, as illustrated in FIG. 4C. In such embodiments, the series of channels can be arranged so that the diameter of the extended channel increases or decreases over the length of the extended telescoping configuration.

Adjustable Electrode within a Tube Embodiment

In another embodiment, the channel may be defined by an outer conductive tube forming a first electrode and a second electrode positioned within the inner void of the outer conductive tube. In some embodiments, the electrodes comprise a "tube within a tube" electrode arrangement of any shaped tubes, such as, but not limited, to circular tubes or polygon tubes. In some embodiments, the inner electrode is placed concentrically within the outer electrode. In some embodiments, the inner electrode is a solid rod. In some embodiments, the inner electrode is planar. In some embodiments, the outer conductive tube comprises a series of spaced ring electrodes. In some embodiments, the inner and outer electrodes are different shapes.

Figure 5A:
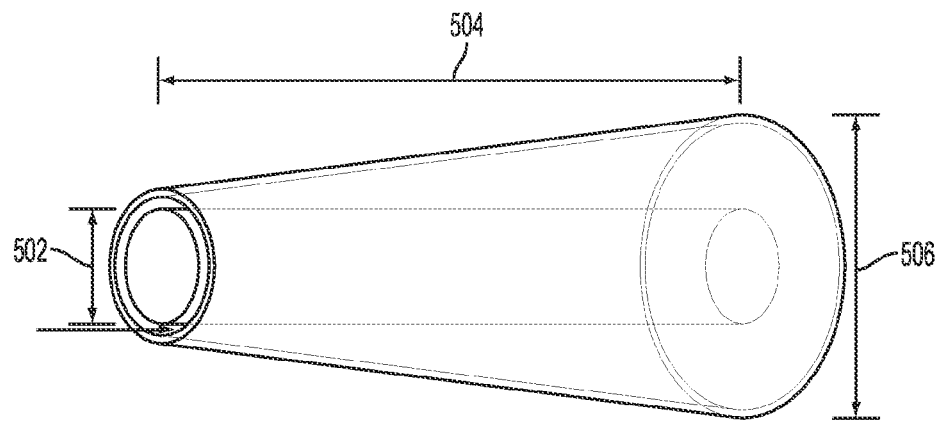
FIG. 5A shows a tube-within-a-tube embodiment where the outer tube is conical and the inner tube has a constant diameter.
Figure 5B:
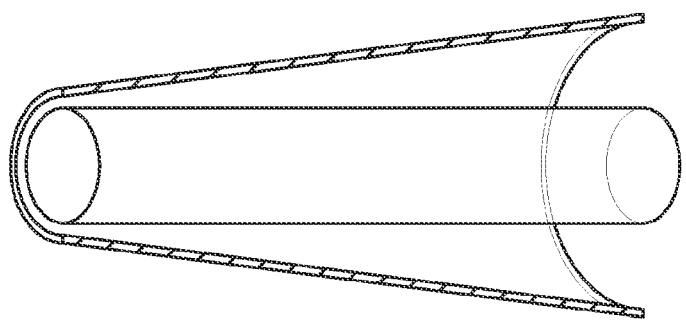
FIG. 5B shows cut-away view of the tube-within-a-tube embodiment where the outer tube is conical and the inner tube has a constant diameter.
Figure 5C:
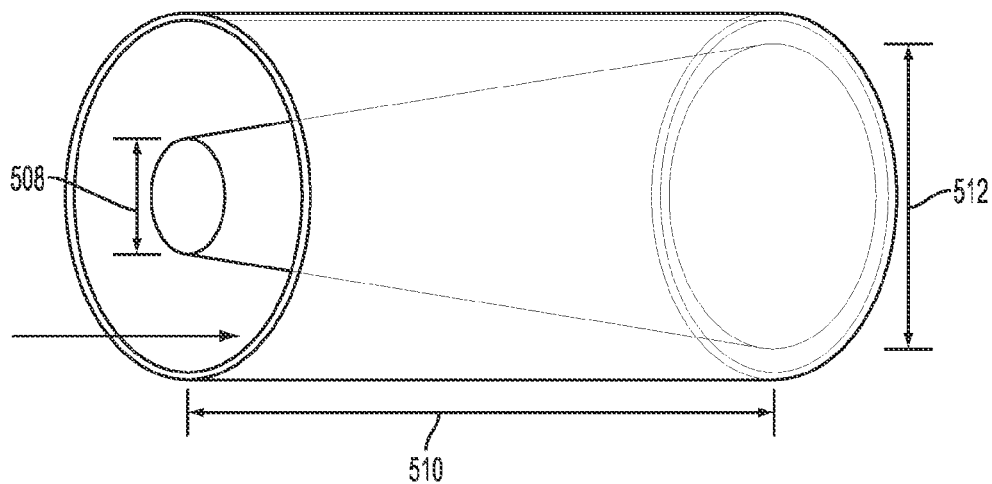
FIG. 5C shows a tube-within-a-tube where the outer tube has a constant diameter and the inner tube is conical.
Figure 5D:
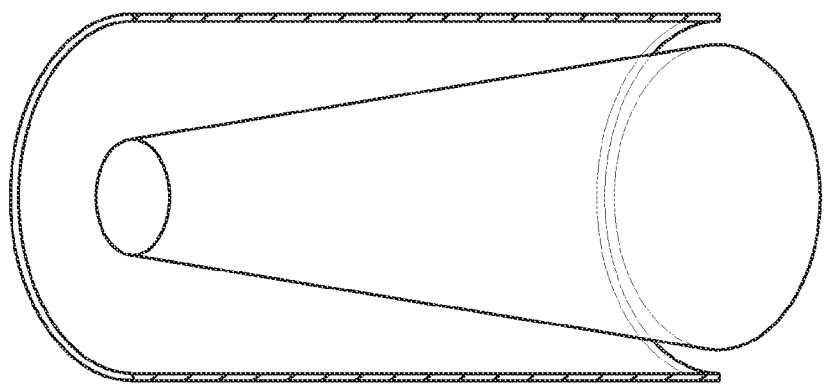
FIG. 5D shows a cut-away view of the tube-within-a-tube where the outer tube has a constant diameter and the inner tube is conical.

In some embodiments, as shown in FIG. 5A, the outer conical electrode can have an increasing diameter over length 504 so that 506 (exit flow diameter) is greater than 502 (inflow diameter). In this embodiment, the inner electrode is tubular with a constant diameter, as shown in FIG. 5B. Conversely, in another embodiment, fluid can flow in the opposite direction so that the channel has a decreasing diameter over length 504 of the channel. In another embodiment, as shown in FIG. 5C, the outer electrode is tubular with a constant diameter and the inner electrode is conical with a diameter that increases over length 510 so that exit flow diameter 512 is greater than inflow diameter 508. The conical shape of the inner electrode is shown in FIG. 5D. Conversely, in another embodiment, the fluid can flow in the opposite direction so that that the diameter of the inner conical electrode decreases over length 510.

In some embodiments, the outer and inner electrodes comprise a series of channels coupled in a telescoping manner, as described above. In some embodiments, the telescoping outer and inner electrodes have an asymmetrical number of telescoping sections or thicknesses, which results in a change in the channel cross-sectional area when extended.

Electrodes

According to various embodiments, the anode and cathode can be made of any electrically conductive material suitable for applying an electrical field across the various gaps described herein, including but not limited to metals such as, but not limited to, steel, aluminum, copper, nickel, titanium and conductive composites or polymers, such as graphite. In some embodiments, the material selected for the anode and cathode are resistant to corrosion, while in other embodiments the material selected is non-corrosive or damage stabilized. In some embodiments, the electrically conductive material may be coated by materials comprising iridium, ruthenium, platinum, rhodium, tantalum, and mixed metal polymers. The electrode material and coating may be selected to minimize the amount of pitting on the electrode and/or the amount of the electrode conductive material or coating which leaches into the aqueous suspension during operation.

In various embodiments, the shape of the anode and cathode can be planar, cylindrical or any other suitable solid, hollow, wire, mesh or perforated shape(s). According to at least some embodiments, as described more fully below, an annulus created between an inner conductive (and in some embodiments metallic) surface of a larger tube and an outer surface of a smaller conductive tube (also metallic according to some embodiments) placed within the larger tube is suitable for its ability to avoid fouling and/or shorting and to maintain a high surface area in a compact design. However, the tubes need not have a circular periphery as an inner or outer tube may be square, rectangular, polygonal, or any other suitable shape according to various embodiments. Moreover, the tube shape does not necessarily have to be the same, thereby permitting tube shapes of the inner and outer tubes to be different in some embodiments. In at least one embodiment, the inner (smaller) conductive tube and outer (larger) conductive tube are concentric tubes, with at least one tube, preferably the outer tube, being provided with a plurality of spiral grooves separated by lands to impart a rifling to the tube. This rifling, according to some embodiments, has been found to decrease build-up of residue on the tube surfaces. In some commercial embodiments, there may be a plurality of inner tubes surrounded by an outer tube to increase the surface contact of the conductors with the microorganisms or to otherwise increase the residence time and/or concentration of electrical current applied to the microorganisms. In some embodiments, the electrodes may comprise wire electrode wrapped in a coil configuration. Either the anode and/or the cathode may be spiral shaped or form one or more rings in the conduit containing the liquid flow.

In other embodiments, however, the use of electrical insulators, such as plastic tubes, baffles, and other devices, can be used to separate a large aggregation device into a plurality of zones, so as to efficiently scale-up the invention for commercial applications.

In performing the method according to certain embodiments, the aqueous suspension containing microorganisms is fed through a channel along fluid flow path between the anode and cathode (i.e., through the gap). According to certain embodiments, power is applied to the anode and cathode to produce an electrical field that aggregates the microorganisms by affecting the surface charge and without causing the cells to be compromised, lysed or disrupted. In various embodiments, the characteristics of the electrical field depend on the composition of the aqueous suspension, the gap dimensions, the electrode materials, the characteristics of the electrical current, and the flow rate.

The apparatus comprises an aqueous suspension disposed between the cathode and anode. According to some embodiments, the aqueous suspension containing microorganisms is caused to flow through the channel using a pump or gravity. In such embodiments, and by way of an electrical conduit, a negative connection is made to the anode, which provides electrical grounding. Further according to such embodiments, a positive electrical input is also delivered by way of a conduit connection in order to provide a positive electrical transfer throughout the cathode. According to such embodiments, when a positive current is applied to the cathode, the positive current then seeks a grounding circuit for electrical transfer, or in this case, to the anode, which allows the completion of an electrical circuit. In this respect, and according to such embodiments, an electrical field is created through a transfer of electrons between the positive and negative surfaces areas, but only when an electrically conductive liquid is present between them. Thus, according to such embodiments, as the liquid medium containing the aqueous suspension is flowed between the surface areas, an electrical transfer from the cathode through slurry to the anode occurs. In other words, as an aqueous suspension containing microorganisms transverses the anode and cathode circuit according to the embodiments described above, the microorganism cells are exposed to an electric field that causes aggregation of the cells or otherwise induces the cells to subsequently aggregate following exposure to the electric field.

A simplified description to illustrate an electrical transfer between two electrical conductive components with a liquid medium containing a living microorganism biomass flowing between them is described below. According to some embodiments, the cathode uses a positive electrical connection point, which is used for positive current input according to some embodiments. According to such embodiments, positive transfer polarizes the entire length and width of the cathode and seeks a grounding source in the anode. In order to complete an electrical circuit, according to such embodiments, the anode includes a grounding connection point, which allows an electrical transfer to occur through aqueous slurry according to some embodiments. In some embodiments, the aqueous slurry includes a liquid medium that contains a nutrient source mainly composed of a conductive mineral content that was used during a growth phase of the microorganism in the aqueous slurry. According to such embodiments, the liquid medium containing the nutrient source further allows positive electrical input to transfer between the cathode through the liquid medium/biomass to the anode, which, according to some embodiments, only occurs when the liquid medium is present or flowing. Additionally, in some embodiments, the amount of electrical voltage and/or current or frequency input can be adjusted based on a matrix formula of grams of microorganism biomass contained in 1 liter of the liquid medium.

Tunable Electrical Field

Figure 6:
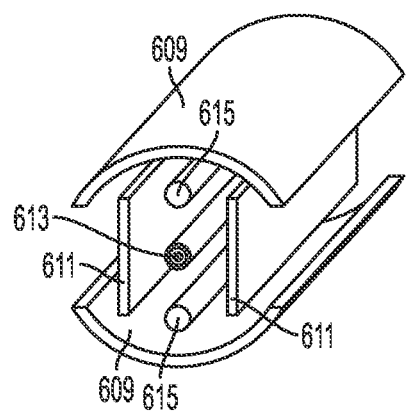
FIG. 6 shows an embodiment with an arrangement of electrodes within a pipe or tube.

In some embodiments, the electrodes within a pipe or tube comprise an arrangement in which the electrodes are capable of changing the cross-sectional shape and area of the electric field within the flow path of the channel, as shown in FIG. 6. In some embodiments, the electrodes comprise at least one cathode 613, at least one anode 609, at least one collector electrode 611, and at least one control electrode 615. The at least one cathode 613 may be solid or hollow. The at least one cathode 613 may be a rod, plate or tube. The at least one cathode 613 may have a circular, oval or polygonal shaped cross-section. The at least one anode 609 may have a semi-circular cross section or a circular cross section. The at least one collector electrode 611 may have a circular, oval, polygonal, curved or v-shaped cross-section. The at least one control electrode 615 may have a circular, oval or polygonal shaped cross-section.

In a configuration with at least one cathode, at least one anode, at least one collector electrode, and at least one control electrode, the current leaving the at least one cathode is simultaneously subjected to two electrostatic fields. One field being positive and the other field being negative. The negative field cooperates with the positive field to compress the current flow of the electrical field, with the ratio between the positive field and negative field controlling how far the electrical field cross-sectional area expands or contracts. In operation, the at least one collector electrode and the at least one anode are maintained at a positive potential with respect to the at least one cathode. The positive potential of the at least one anode is larger than the potential of the at least one collector electrode. The at least one control electrode is maintained at a negative potential with respect to the at least one cathode.

The ratio between the positive field and the negative field may be changed by increasing or decreasing the potential of the at least one collector electrode and/or the at least one control electrode, thus affecting the cross-sectional area of the electrical field. With the ability to increase or decrease the cross-sectional area of the electrical field, the electrical field can be focused to a desired size or a desired location within the flow path channel. This allows for a more focused and finely tuned application of electricity to the algae suspension, which in turn allows for better manipulation and control of the algal flow. Decreasing the negative potential of the at least one control electrode allows the current flow from the at least one cathode to the central portion of the at least one collector electrode, or to the edge of the at least one collector electrode, or beyond the at least one collector electrode to the at least one anode. In a similar manner, the cross-sectional area of the current flow from the at least one cathode to the at least one anode can be contracted by increasing the negative potential of the at least one control electrode.

Increasing the positive potential of the at least one collector electrode can also expand the cross-sectional area of current flowing from the at least one cathode to a larger surface area of the at least one collector electrode. Decreasing the positive potential of the at least one collector electrode can also contract the cross-sectional area current flowing from the at least one cathode to a smaller surface area of the at least one collector electrode. Decreasing the positive potential of the at least one collector electrode when the negative potential of the at least one control electrode is also decreased will expand the cross-sectional area of the current flow from the at least one cathode to the at least one anode, and decrease the current flow from the at least one cathode to the at least one collector electrode. In a similar manner, increasing the positive potential of the at least one collector electrode when the negative potential of the at least one control electrode is decreased will contract the cross-sectional area of the current flow from the at least one cathode to the at least one anode, and expand the cross-sectional area of the current flow from the at least one cathode to the at least one collector electrode.

Figure 7A:
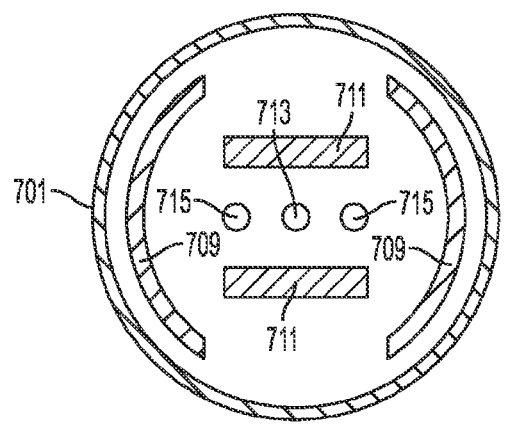
FIG. 7A shows a straight-on view of an embodiment of electrodes within a pipe or tube.
Figure 7B:
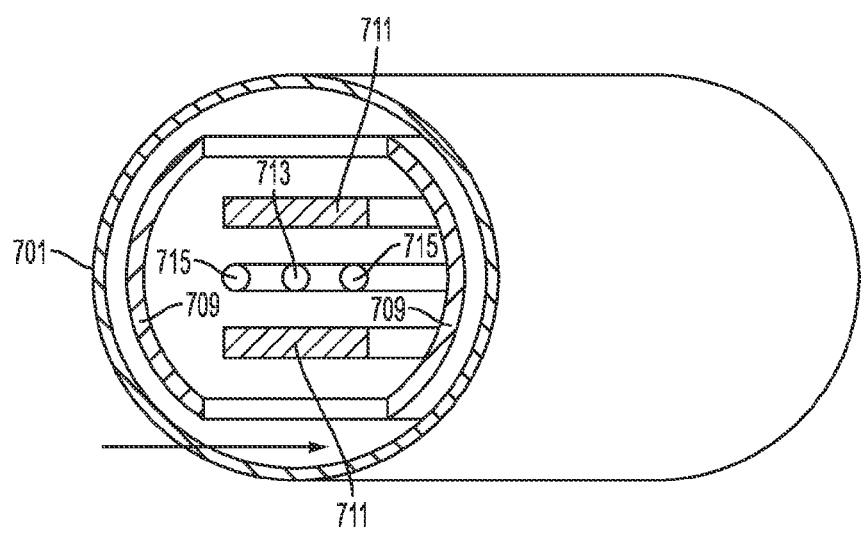
FIG. 7B shows a side view of an embodiment of electrodes within a pipe or tube.

In one exemplary embodiment, as shown in FIGS. 7A-B and 8A-C, two curved plate anodes 709 are disposed opposite each and on the inner surface of a tube or pipe shaped housing 701 in FIGS. 7A-B. The tube or pipe shaped housing 701 may be made from a non-conductive material. Disposed between the two anodes 709 are a vertical pair of parallel plate collector electrodes 711. A circular cross-section shaped rod cathode 713 is centered between the anodes 709 and the collector electrodes 711. Two circular rod shaped control electrodes 715 are disposed on each side of the cathode 713 between the cathode 713 and one of the anodes 709. In some embodiments, the anodes 709 may be electrically independent of each other and supplied current by individual connections. A flow path for an aqueous suspension is provided between the interior surface of the tube or pipe shaped housing and the exterior surfaces of the various electrodes.

Figure 8A:
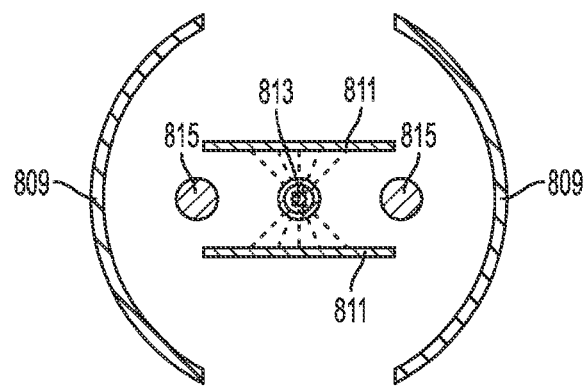
FIGS. 8A-C each show an embodiment with an arrangement of electrodes within a pipe or tube and various cross-sectional areas of electrical fields shown in dashed lines.
Figure 8B:
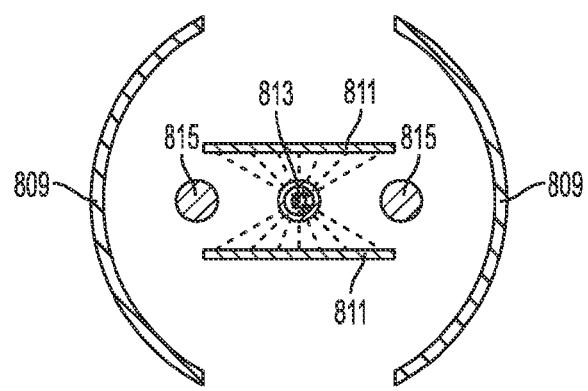
Figure 8C:
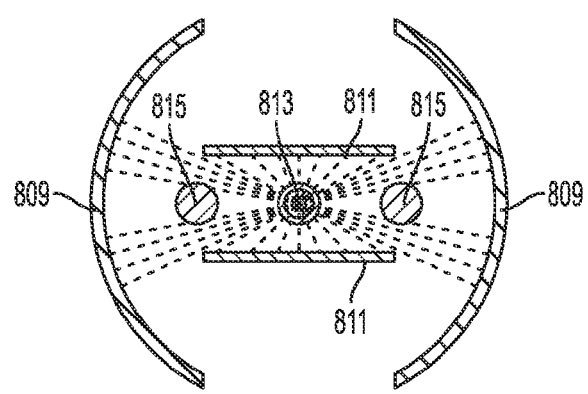

As shown in FIG. 8A-C, the potential applied to the collector electrodes 811 and/or the control electrodes 815 can manipulate the cross-sectional area of the electrical field. In a balanced condition, the control electrodes 815 may be biased negatively to an extent sufficient to compel the current leaving the cathode 813 to travel to the collector electrodes 811 and not reach the anodes 809. For the balanced condition neither a high positive potential of the collector electrodes 811 nor a high negative potential on the control electrodes 815 is necessary. As the collector electrodes 811 are made more positive or the control electrodes 815 are made more negative than the balanced condition, the cross-sectional area of the electrical field expands out towards the edge of the collector electrodes 811. A decrease in the positive potential applied to the collector electrodes 811 or a further decrease in the negative potential applied to the control electrodes 815 results in the cross-sectional area of the electrical field expanding beyond the surface of the collector electrodes 811 to the anodes 809. Similarly, manipulating the collector electrodes 811 and control electrodes 815 in an opposite manner will contract the cross-sectional area of the electrical field. Variations in the electrical field are expressed as dashed lines in the FIGS.

Figure 9:
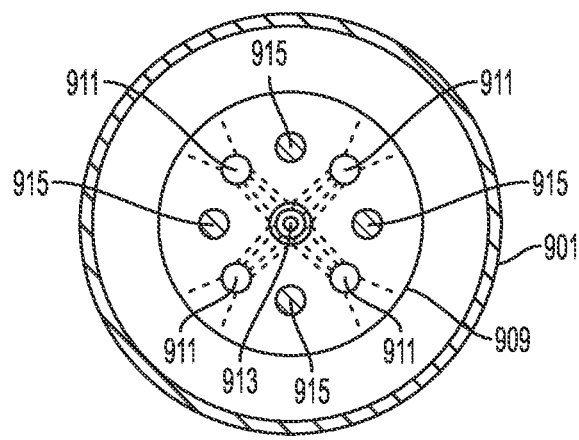
FIG. 9 shows an embodiment with an arrangement of electrodes within a pipe or tube and a cross-sectional area of an electrical field shown in dashed lines.
Figure 10:
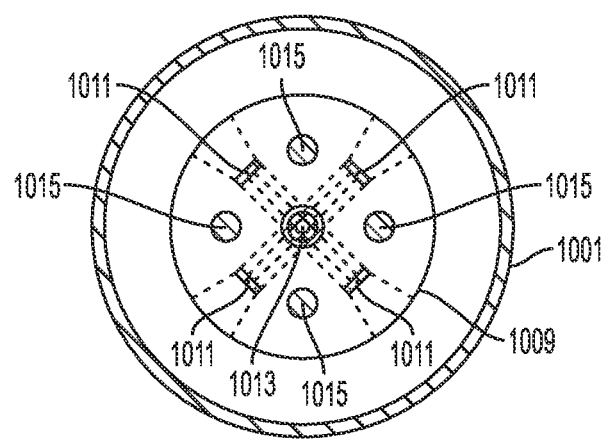
FIG. 10 shows an embodiment with an arrangement of electrodes within a pipe or tube and a cross-sectional area of an electrical field shown in dashed lines.

In other embodiments illustrated by FIGS. 9 and 10, the anode 909, 1009 comprises a round, conductive tube or a series of conductive rings, and the cathode 913, 1013 is a circular rod disposed concentrically within the anode 909, 1009. The anode 909, 1009 may be disposed within a tubular housing or piping 901, 1001. The collector electrodes 911, 1011 comprise four rods 911 or plates 1011 disposed with even spacing around the cathode 913, 1013, and between the anode 909, 1009 and the cathode 913, 1013. The control electrodes 915, 1015 comprise four rods disposed with even spacing around the cathode 913, 1013, and between the anode 909, 1009 and the cathode 913, 1013. A flow path for an aqueous suspension is provided between the inner surface of the anode 909, 1009 and the exterior surfaces of the other electrodes. When the potential applied to the collector electrodes 911, 1011 and the control electrodes 915, 1015 is manipulated as previously described above the current flowing from the cathode 913, 1013 extends to the collector electrodes 911, 1011 and beyond to the anode 909, 1009 in a plurality of bands equal to the number of collector electrodes. The number of collector electrodes and control electrodes are equal, and the number of electrodes is limited only by the physical dimensions of the electrodes and space available within the tubular anode.

Figure 11:
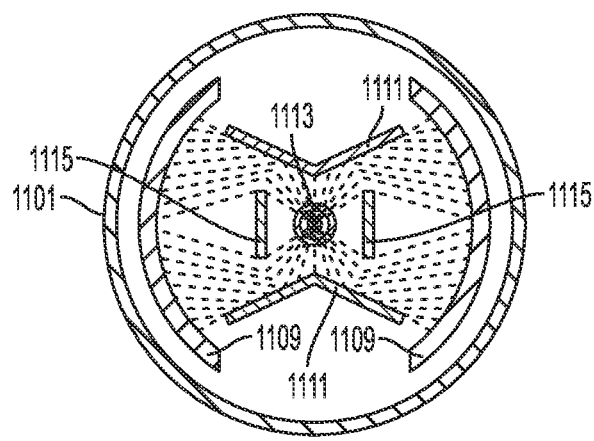
FIG. 11 shows an embodiment with an arrangement of electrodes within a pipe or tube and a cross-sectional area of an electrical field shown in dashed lines.

In another exemplary embodiment illustrated by FIG. 11, the anode 1109 comprises two curved plates disposed opposite each other and within the inner surface of a tube or pipe 1101. The cathode 1113 comprises a circular cross-section shaped rod centered between the anodes 1109. The collector electrodes 1111 comprise a vertical pair of plates with a v-shaped cross-section disposed between the anodes 1109 and on opposing sides of the cathode 1113. The two control electrodes 1115 plates are disposed on each side of the cathode 1113 between the cathode 1113 and one of the anodes 1109. A flow path for an aqueous suspension is provided between the inner surface of the anode 1109 and the exterior surfaces of the other electrodes. When the potential applied to the collector electrodes 1111 and the control electrodes 1115 is manipulated as previously described above, the cross-sectional area of the electrical field is changed.

Figure 12:
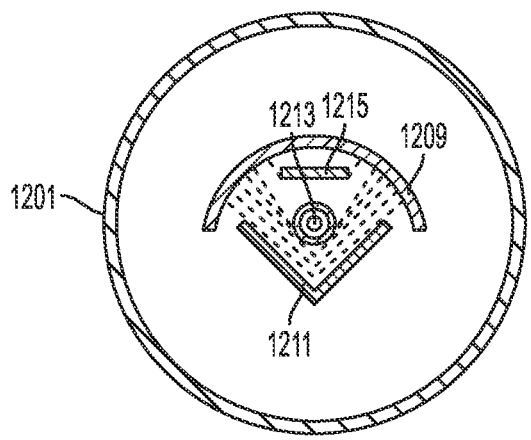
FIG. 12 shows an embodiment with an arrangement of electrodes within a pipe or tube and a cross-sectional area of an electrical field shown in dashed lines.

In another exemplary embodiment as shown by FIG. 12, the anode 1209 comprises a single curved plate. The collector electrode 1211 comprises a plate with a v-shaped cross-section disposed opposite the anode 1209. The cathode 1213 comprises a circular cross-section shaped rod centered between the anode 1209 and the collector electrode 1211. The control electrode 1215 comprises a flat plate disposed between the cathode 1213 and the anode 1209. A flow path for an aqueous suspension is provided within a tube or pipe shaped housing which houses the electrodes, and particularly between the anode 1209 and collector electrode 1211. When the potential applied to the collector electrodes 1211 and the control electrodes 1215 is manipulated as previously described above, the cross-sectional area of the electrical field is changed.

Figure 13A:
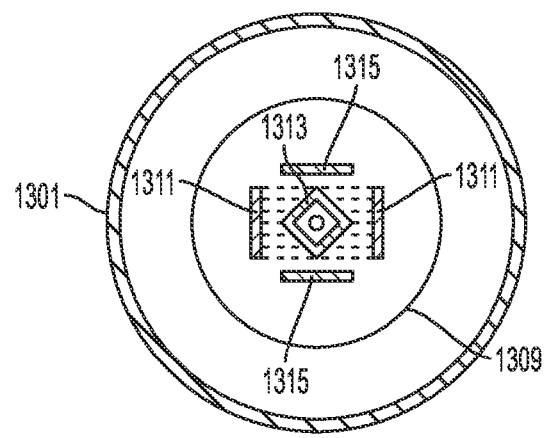
FIGS. 13A-C each show an embodiment with an arrangement of electrodes within a pipe or tube and various cross-sectional areas of electrical fields shown in dashed lines.
Figure 13B:
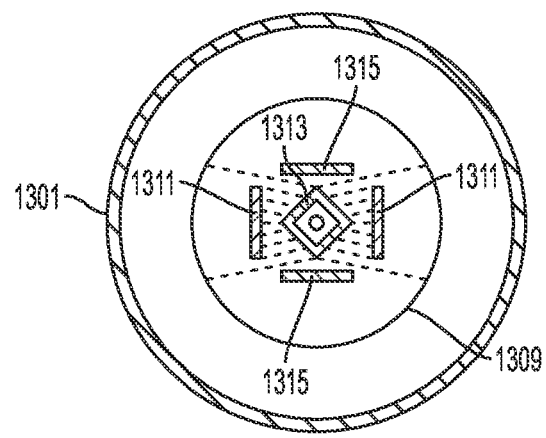
Figure 13C:
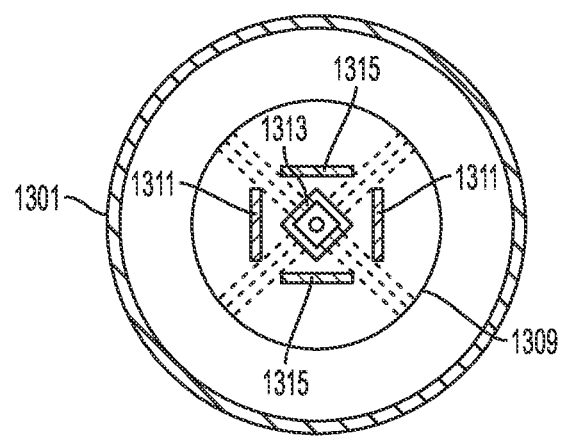

In another exemplary embodiment shown in FIGS. 13A-C, the anode 1309 comprises a round, conductive tube or series of conductive rings, and the cathode 1313 is a square rod disposed concentrically within the anode 1309. The collector electrodes 1311 comprise a pair of flat plates disposed on opposite sides of the cathode 1313. The control electrodes 1315 comprise a pair of flat plates disposed on opposite sides of the cathode. A flow path for an aqueous suspension is provided between the interior surface of the anode 1309 and the exterior surfaces of the other electrodes. The entire set is located inside a non-conductive tubular housing 1301. When the potential applied to the collector electrodes 1311 and the control electrodes 1315 is manipulated as previously described above, the cross-sectional area of the electrical field is changed.

Figure 14A:
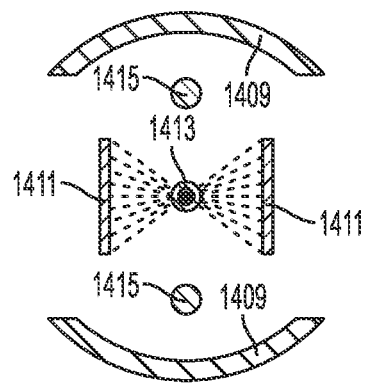
FIGS. 14A-C each show an embodiment with an arrangement of electrodes within a pipe or tube and various cross-sectional areas of electrical fields shown in dashed lines.
Figure 14B:
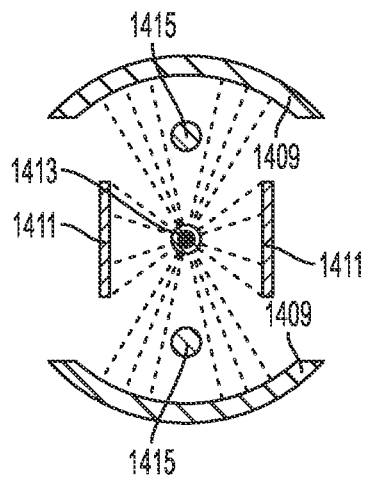
Figure 14C:
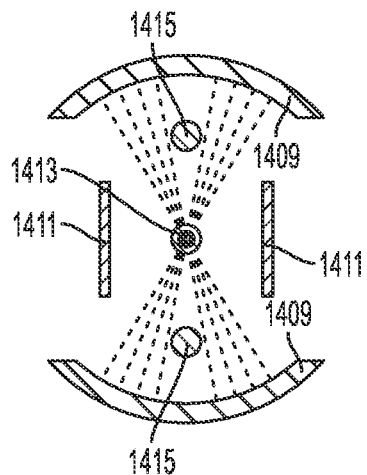

In another exemplary embodiment illustrated by FIG. 14A-C, anode 1409 comprises two curved plates disposed opposite each other. Cathode 1413 comprises a circular cross-section shaped electrode centered between anodes 1409. Collector electrodes 1411 comprise a vertical pair of plates spaced evenly around cathode 1413 and between anodes 1409 and cathode 1413. Two control electrodes 1414 are disposed on each side of cathode 1413 between cathode 1413 and one of anodes 1409. A flow path for an aqueous suspension is provided between the interior surface of the anode 1409 and the exterior surfaces of the other electrodes. When the potential applied to the collector electrodes 1411 and the control electrodes 1415 is manipulated as previously described above, the cross-sectional area of the electrical field is changed.

In some embodiments, as mentioned above, the foregoing electrical transfer through the living microorganism is achievable due to nutrients containing electrically conductive minerals suspended within the aqueous suspension or the salinity level of the aqueous suspension.

In at least one embodiment, the flow rate through the gap volume (i.e., the portion of channel 112 in the electric field at the gap distance 114) is 0.1 ml/second per ml of gap volume. In other embodiments, however, the flow rate through the gap volume is at least 0.5 ml/second per ml of gap volume while in other embodiments the flow rate through the gap volume is at least 1.0 ml/second per ml of gap volume. In still other embodiments, the flow rate through the gap volume is at least 1.5 ml/second per ml of gap volume. In yet other embodiments, the flow rate through the gap volume exceeds 1.5 ml/second per ml of gap volume. In at least one additional embodiment, the flow rate can be controlled by controlling the pressure using a pump or other suitable fluid flow mechanical devices. In other embodiments, the flow rate is affected by the varying dimensions of the flow path channel.

Characteristics of Electrical Power

In some embodiments, the electrical field is sustained at a constant or continuous level with direct current. In some embodiments, the electrical field is varied by using an alternating current or can be pulsed on and off repeatedly. Whether the electrical field is continuous, varying, or pulsed, the amplitude and/or intensity of the electrical field is selected to induce aggregation of the microorganisms within the aqueous suspension without lysing or disrupting the cell membrane of the microorganisms. According to such embodiments, voltages can be higher and peak amperage lower while average amperage remains relatively low. In such embodiments, this condition or controlled circumstance reduces the energy requirements for operating the apparatus and reduces wear on the anode and cathode pair or pairs. In some embodiments, the frequency of the electrical field pulse is at least about 500 Hz, 1 kHz, 2 kHz, 30 kHz, 50, kHz, 80, kHz, or 200 kHz. In some embodiments, the electrical pulse duration ranges from 1 nanosecond to 100,000 nanoseconds, 1 to 1,000 nanoseconds, 1 to 500 nanoseconds, or 10 to 300 nanoseconds; allowing for frequencies of about 10 kHz to 1,000,000 kHz. Ranges for the pulse frequency can be any combination of the foregoing maximum and minimum frequencies according to various embodiments. In some embodiments, the use of nanosecond pulses reduces the thermal effects on the aqueous suspension and the production of excess free charges in the aqueous slurry, which may limit the galvanic processes that lead to corrosion, pitting, and leaching of electrode metals. In some embodiments, the use of a pulsed electrical field reduces the overall power requirements of the apparatus, system and/or method, compared to the use of a constant or continuous electrical field.

In some embodiments, the electrical pulses are provided by a pulse generator. In some embodiments, the pulse shape is rectangular, trapezoidal, exponentially decaying, unipolar or bipolar. In further embodiments, the pulse generator produces two different pulse types. In still further embodiments, the pulse generator produces at least two different pulse types. In some embodiments, the pulses are provided in a continuous manner and each pulse is identical in pulse amplitude, pulse duration, pulse shape, and pause duration between pulses. In some embodiments, the pulses are provided in continuous manner and at least one of the pulse amplitude, pulse duration, pulse shape, and pause duration between pulses varies.

Figure 15A:
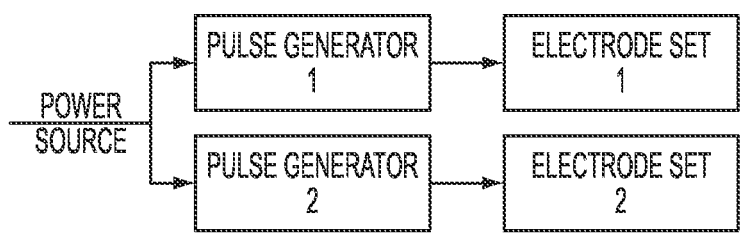
FIG. 15A shows a diagram of a system with multiple pulse generators and multiple electrode sets.
Figure 15B:
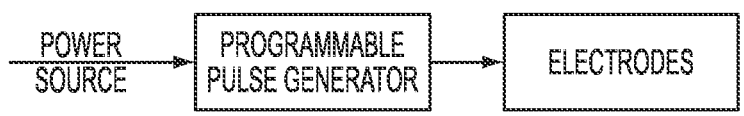
FIG. 15B shows a diagram of a system with a programmable pulse generator.

In further embodiments, the pulse amplitude and duration are identical in each pulse, but the duration of the pause between pulses varies. In further embodiments, the pulses alternate between two different pulses in a pattern, such as but not limited to long pulse then short pulse. In further embodiments, the pattern of pulses repeat a pattern more complex than simply alternating between two pulse types (similar to a Morse code transmission), such as but not limited to short pulse, short pulse, long pulse, short pulse, long pulse, long pulse. In further embodiments, the pattern of pulses comprises more than two pulse types. In some embodiments, multiple pulse generators and multiple electrode sets are used, as shown in FIG. 15A. In further embodiments, the varying pulse patterns are programmable into the pulse generator. FIG. 15B shows an exemplary scheme of an apparatus that includes a programmable pulse generator. In still further embodiments, the pulse pattern program utilized by the pulse generator is selected by a computerized controller based on sensory input such as, but not limited to, turbidity of the aqueous suspension, density of the aqueous suspension, composition of the aqueous suspension, and flow rate.

In some embodiments, the power supply provides alternating current while in other embodiments the power supply provides direct current. Moreover, in some embodiments, the anode and the cathode pair are fixed during aggregation while in other embodiments the anode/cathode pair or circuit alternates during aggregation.

In various embodiments, the average amperage is at least 1 amp, 5 amps, 10 amps, 50 amps, or even at least 100 amps. According to at least some embodiments, the maximum amps can be less than 200 amps, less than 100 amps, less than 50 amps, or less than 10 amps. As with pulse frequency and the like, the range of amperage can be any range from the foregoing maximum and minimum amperages according to various embodiments. The current density (amps/cm$^2$) is defined as the flow of the electric charge per surface area of the electrodes. The current level and dimensions of the electrode may be selected together in a manner to optimize the current density, which is a factor in the pitting and/or leaching of the electrode metals.

Similarly, according to various embodiments, the voltage can be at least 1V, 10V, 100V, 1 kV, 20 kV, 50 kV, 100 kV, or 500 kV. Again, the range of voltage can be any range of the foregoing maximum and minimum voltages according to various embodiments. The voltage of the electrical field may be selected in conjunction with the gap distance of the flow path to produce an optimal electrical field for aggregating microorganisms without lysing or disrupting the cell membranes. In some embodiments, the amplitude (the applied voltage divided by distance between electrodes) of the electrical fields to which the aqueous slurry is exposed to may range from 0.05 V/cm to 1,000 kV/cm. In some embodiments, the amplitudes of the electrical fields to which the aqueous slurry is exposed to may range from 0.1 to 100,000 kV/cm, 10 to 1,000 kV/com, 50 to 500 kV/cm, or 100 to 400 kV/cm.

The peak power of the electrical field may be at least 500 kW, or at least 1 megawatt. The energy delivered by the electrical field may range from 0.1 to 100 joules, or 1 to 10 joules. Depending on the composition of the aqueous slurry, residence time, configuration of the electrodes, and configuration of the flow path channel, electrical field may be tuned to induce aggregation of the microorganisms in 1-60 seconds, less than 5 minutes, less than 15 minutes, less than minutes, or less than one hour.

Additional details on Tube Within a Tube Embodiment

Figure 16:
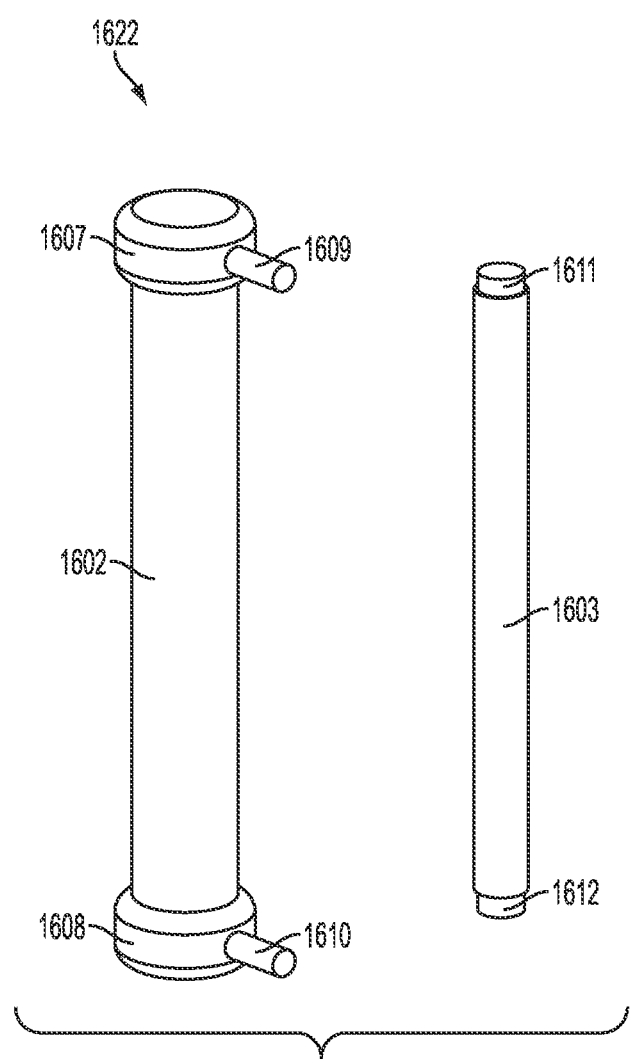
FIG. 16 shows an exemplary embodiment of a disassembled tube-within-a-tube configuration.

As illustrated in FIG. 16, apparatus 1622 is comprised of a "tube within a tube" configuration according to some embodiments. According to some embodiments, FIG. 16 illustrates a disassembled aggregation device showing a first (smaller) conductive tube 1603 (hereinafter cathode 1603, although conductive tube 1603 may also be the anode or switch between anode and cathode according to various embodiments) that is configured to be placed in a second (larger) conductive tube 1602 (hereinafter anode 1602, although conductive tube 1602 may also be the cathode or switch between anode and cathode according to various embodiments). In some embodiments, the outer anode tube 1602 includes a pair of containment sealing end caps 1607 and 1608. In such embodiments, sealing end cap 1607 provides an entry point 1609 used to accept an aqueous suspension. Following the transition of the aqueous suspension through anode 1602 according to various embodiments, the opposing end cap 1608 provides an exit point 1610 to the outward flowing aqueous suspension.

With continued reference to FIG. 16, in some embodiments, the inner cathode tube 1603 includes sealed end caps 1611 and 1612 to prevent liquid flow through the center of the tube and to divert the flow between the inner surface of anode 1602 and the outer surface of cathode 1603, thereby forming a channel or annulus between anode 1602 and cathode 1603. In some embodiments, the channel can be sized and configured as described above. According to the foregoing embodiments, the use of a "tube within a tube" configuration is particularly advantageous for avoiding fouling or shorting by the microorganisms in the aqueous suspension.

Figure 17:
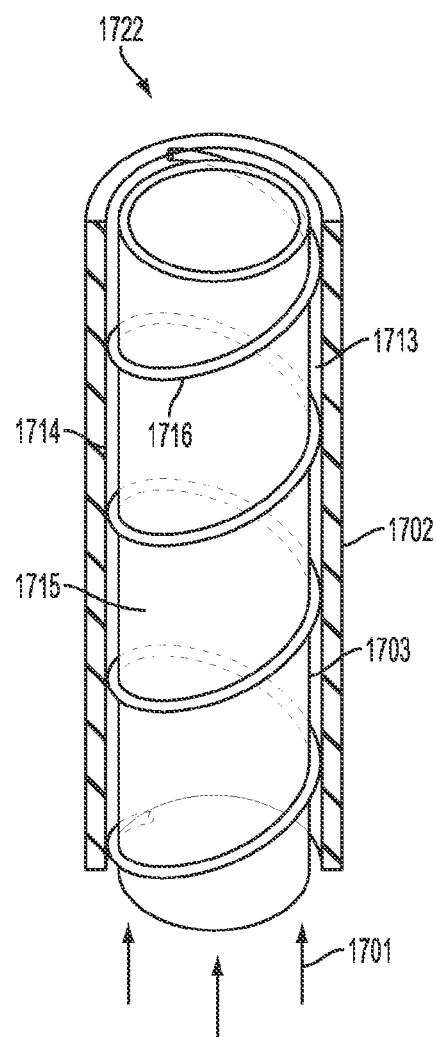
FIG. 17 shows an exemplary embodiment of a disassembled tube-within-a-tube configuration.
Figure 18A:
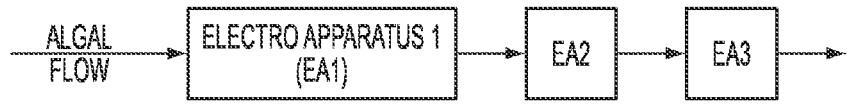
FIGS. 18A-D each show exemplary embodiments of series systems, parallel systems, and series/parallel systems with various electric and acoustic devices.
Figure 18B:
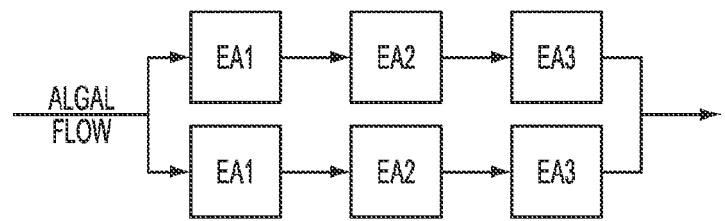
Figure 18C:
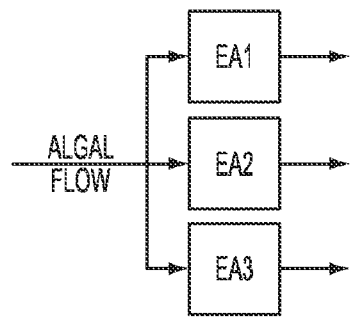
Figure 18D:
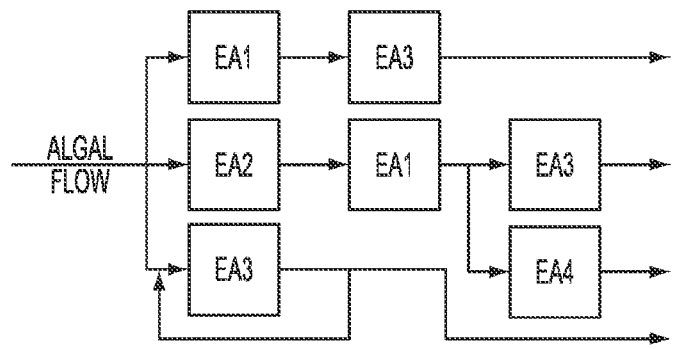

Turning now to FIG. 17, an alternative embodiment of apparatus 1722 is illustrated. As seen in FIG. 17, in some embodiments, an insulative spacer 1716 is positioned in the channel between anode 1702 and cathode 1703 to cause spiraling fluid flow. In such embodiments, insulative spiraling isolator spacer 1716 serves as a liquid seal between the two wall surfaces 1714 and 1715 with the thickness of the spacer preferably providing equal distance spacing between anode 1702 and cathode 1703. According to some embodiments, the spacing and directional flow can cause the fluid flow path to complete a three hundred and sixty degree transfer of electrical current around anode 1702 and cathode tube 1703. In some further embodiments, the spacer 1716 can also help prevent contact between anode 1702 and cathode 1703, which prevents shorting or fouling the anode and cathode pair and forces electrical current through the liquid medium. According to various embodiments, the spiraling isolator 1716 also provides a gap 1713 between the two wall surfaces 1714 and 1715 allowing a passage way for a flowing aqueous suspension 1701. In some embodiments, the spiraling directional flow further provides a longer transit duration or residence time, which in turn provides greater electrical exposure to the flowing aqueous suspension 1701 thus increasing aggregation efficiency at a lower per kilowatt hour consumption rate. In some embodiments, the width of the gap 1713 is uniform over the length of the passage way. In some embodiments, the width of the gap 1713 increases or decreases over the length of the passage way. According to various embodiments, any suitable material can be used as a spacer. According to some embodiments, ceramic, polymeric, vinyl, PVC plastics, bio-plastics, vinyl, monofilament, vinyl rubber, synthetic rubber, or other non-conductive materials are used.

Multiple Path Embodiments

A plurality of anode and cathode circuits, according to some embodiments, are configured in parallel having a common upper manifold chamber, which receives an in flowing biomass a through entry port. According to such embodiments, once entering into the upper manifold chamber, the biomass a makes a downward connection into each individual anode and cathode circuit through entry ports, which allow a flowing connection, or a fluid connection, to the sealing end caps. According to such embodiments, it is at this point where the flowing biomass (i.e., the aqueous suspension of microorganisms) enters into the anode and cathode circuits. Further according to such embodiments, once transiting through the individual circuits, which in some embodiments comprise a spiral flow path while in other embodiments a straight or other configured fluid flow path is contemplated, the flowing biomass exits into a lower manifold chamber where the biomass is then directed to flow out of the apparatus (system) through an exit point.

As described herein, the flow path of each anode and cathode circuit may have different characteristics, such as but not limited to, height, width, diameter, length, electrode material, electrical field amplitude/intensity, electrical field cross section, and electrical pulse frequency/duration. Depending on the end use of the apparatus output, such as but not limited to fuel, food, feed, fertilizer, cosmetics and pharmaceuticals, the degree of aggregation and/or the electrode material requirements may be different. For example, if the resulting aggregated microorganisms being sold as whole algae may require different processing and ending solids percent than aggregated microorganisms that will go through further downstream processing, such as an extraction process. In some embodiments, the electrode materials may have a different effect on the microorganisms, therefore requiring microorganisms for specific products to be aggregated with electrodes of a specific material. In some embodiments, the differently configured flow paths with parallel anode and cathode circuits would allow the aqueous suspension to be split into separate streams for concurrent processing for different outputs. The differently processed streams may exit the anode and cathode circuits into different separation tanks to maintain segregation before going on to further processing. In other embodiments, the plurality of anode and cathode circuits with differently configured flow paths may be connected in series, allowing the aqueous suspension to go from one anode and cathode circuit to the next in a series of varying conditions without adjusting the equipment. Embodiments of the various configurations are illustrated in FIGS. 18A-D. Each different EA (electro apparatus) designates a different electric aggregating device. Any of the ° representative aggregating systems described in this specification can be used as a particular EA shown in the FIGS. 18A-D.

In some embodiments, the plurality of anode and cathode circuits comprise the same configuration and are connected in series to increase the residence time of the aqueous suspension within the electrical field. In further embodiments, the apparatus may switch between a parallel connection configuration and a series connection configuration. In some embodiments, the plurality of anode and cathode circuits are all connected in parallel or all connected in series. In some embodiments, the plurality of anode and cathode circuits are connected in a combination of parallel and series configurations. Non-limiting examples of such embodiments with a combination of series and parallel connections include: a plurality of groups of circuits connected in parallel wherein each group of circuits consists of at least two circuits connected in a series; half of the circuits connected in parallel and the other half of the circuits connected in a series; and a plurality of groups of circuits connected in series wherein each group of circuit consists of at least two circuits connected in parallel.

According to some embodiments, the various system embodiments discussed above are adjustable, and can be set up with various flow rates, voltage, amperage, electrical pulse frequency/duration, electrical field amplitude/intensity, flow path width, flow path height, flow path diameter, flow path length and/or variable temperatures. According to some embodiments, the microorganisms in suspension, enter into an electrical field and are subjected to a current input for a prescribed transit or residence time within the system (which can be adjusted according to flow rate, the use of spiraled or rifled circuits, or flow path dimensions) which dictates the degree to which the microorganisms are aggregated. According to some embodiments, various determining factors for this method include, but are not limited to:

The amount of energy input (total wattage as a combination of volts and amps);

The frequency in which the electrical input is applied, and duration in which the electrical input is applied;

The type of electrical input applied, such as direct current, alternating current or electrical pulses;

The flow path length (e.g., a rifled interior circuit can have closer rifle spacing for a longer residence or duration flow or electrical field exposure time, a larger rifle spacing for a shorter duration flow or electrical field exposure time, or a telescoping arrangement that can extend and contract in length);

The electrodes can have a smaller gap for longer duration or electrical field exposure time or field strength, or a larger gap for a shorter duration flow or electrical field exposure time or field strength;

The electrode materials, such as steel, aluminum, copper, titanium, nickel, graphite, or conductive polymers, and any coatings on the electrode materials;

A combination of the closer/larger rifle spacing, with a larger/smaller electrode gap;

The concentration of the microorganism culture; and/or

The pH and the salinity of the culture.

According to various embodiments, the longer the total transit or residence time, which can be determined by an adjustable flow rate or flow path dimensions, in combination with higher electrical input, provides greater electrical field exposure to the aqueous suspension. In some embodiments, when setting lower electrical input and higher flow rate parameters, provides a lesser electrical field exposure.

In some embodiments, the use of electrical fields is used to aggregate the microorganisms of an aqueous suspension. For example, microorganisms are grown in a liquid medium. According to some embodiments, the microorganisms are grown in a growth chamber. In some embodiments, a growth chamber may comprise or be comprised of a reactor, a photobioreactor, a pond, or a fermenter. In other embodiments, the microorganisms may be grown in a natural or outdoor environment. For example, according to some embodiments, the growth chamber can be any body of water or container or vessel in which all requirements for sustaining life of the microorganisms are provided. Examples of growth chambers include, but are not limited to, an open pond, a trough, a tube, a bag, or an enclosed growth tank. When added to the aggregation device, the microorganisms are generally in the form of a live slurry (also referred to herein as "biomass") according to certain embodiments. In some embodiments, the live slurry is an aqueous suspension that includes microorganisms, water and nutrients such as an algal culture formula comprising Guillard's 1975 F/2 algae food formula (0.82%

Iron, 0.034% Manganese, 0.002% Cobalt, 0.0037% Zinc, 0.0017% Copper, 0.0009% Molybdate, 9.33% Nitrogen, 2.0% Phosphate, 0.07% Vitamin B1, 0.0002% Vitamin B12, and 0.0002% Biotin) or a variation thereof, that provides nitrogen, vitamins and essential trace minerals for improved growth rates in freshwater and marine microorganisms. In various embodiments, any suitable concentration of microorganisms and sodium chloride, fresh, brackish or wastewater can be used, such that the microorganisms grow in the aqueous suspension.

According to some embodiments, the microorganisms may be harvested by drawing the aqueous microorganism slurry from the growth chamber using various techniques. In at least one embodiment, the method of aggregating microorganisms can be carried out by periodically drawing microorganisms from a growth chamber in a manner that maintains a steady rate of growth. In such embodiments, steady state growth can be achieved by drawing microorganisms at a rate of less than half the microorganism mass per unit time that it takes for the microorganism to double. In one embodiment, microorganisms are harvested at least as often as the doubling time of the microorganism. In other embodiments, however, the microorganism are harvested at least twice during the doubling time of the microorganism. In various embodiments, the doubling time will depend on the microorganism type and growth conditions but can be as little as 6 hours to several days.

The method continues, according to some embodiments, through the use of cavitation. For example, according to such embodiments, prior to aggregation, the slurry can optionally be processed using cavitation and/or heating. As the method continues, the slurry is then aggregated using an electrical field as described herein and according to various embodiments disclosed herein.

In some embodiments, the aqueous slurry is then delivered to the aggregating apparatus using any means, such as, but not limited to, gravity or a liquid pump. As the method continues according to various embodiments, the aqueous microorganism slurry is flowed via a conduit into an inlet section of an anode and cathode circuit of an aggregation device using any suitable device or apparatus, e.g., pipes, canals, or other conventional water moving apparatus(es). In some embodiments, a growth chamber or reactor is operably connected to the aggregating apparatus such that the microorganisms within the growth chamber or reactor can be transferred to the apparatus as discussed above.

According to some embodiments, after the microorganisms are aggregated, the aggregated slurry is dewatered. In such embodiments, dewatering is carried out by separating a portion of the aqueous medium from the aggregated microorganisms using various techniques. In one embodiment, for example, the treated, aggregated microorganisms can be harvested from the top of the tank such as by skimming or passing over a weir, where they can be recovered and/or further processed. In such embodiments, the aggregated microorganisms can float to the surface by creating a bubble stream, either by cavitation of the creation of microbubbles from a microbubble generator or fluidic oscillator, and impinging the bubbles beneath the aggregated microorganisms to cause them to rise to the surface in a froth. Further according to such embodiments, a skimming device is then used to harvest the froth floating on the surface of the liquid column. The remaining liquid (e.g., water) can be filtered and returned to the growth chamber (recycled) or removed from the system (discarded) according to various embodiments. In an alternative embodiment, the aggregated microorganisms may be denser than the liquid medium and allowed to sink to the bottom of a settling tank. In such embodiments, the aggregated microorganisms can be collected in a gravity settling tank and the clarified water can be recycled. In some embodiments, the aggregated microorganisms are separated by a foam fractionation device. The foam fractionation device receives the aqueous suspension containing aggregated microorganisms, and creates a gas/liquid mixture in a liquid chamber by injecting a gas and producing bubbles/microbubbles. The bubbles/microbubbles cause aggregated particles of a threshold size to float to the surface of the liquid chamber and form a foam which may be collected. Any other conventional technique for removing particles, such as filtering, settling, flocculation, centrifugation or other particle aggregation technique may be used, either before or after, in conjunction with the techniques of the present invention.

Multiple Pass Embodiments

Figure 19:
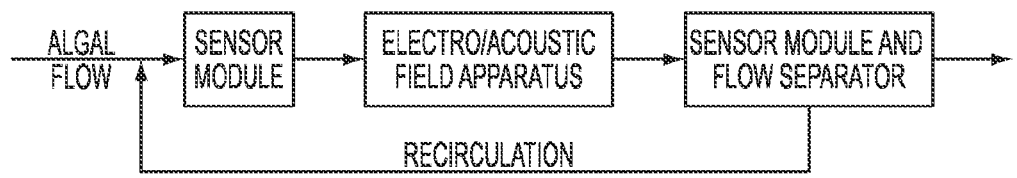
FIG. 19 shows an exemplary system where the suspension exiting the electrical field may be recycled back into the apparatus for further treatment.

In some embodiments, at least a portion of the aqueous suspension exiting the electrical field may be recycled for further exposure to the electrical field for aggregation. Such a system is illustrated in FIG. 19. A system with multiple passes of at least a portion of the aqueous suspension through the electrical field increases residence time for a device to achieve a desired level of aggregation without adjusting the flow path characteristics. Multiple passes could also achieve the same results with less physical equipment (shorter pipes, fewer electrodes, etc.). In some embodiments, the multiple pass system may run the entire volume of the aqueous suspension through the electrical field multiple times before treating a new volume of aqueous suspension in a batch process. In another embodiment, the multiple pass system may bleed off a first portion of the aqueous suspension to be mixed with a volume of untreated aqueous suspension and recirculated through the electrical field in a continuous recycle method, while a second portion continues to the separation device or tank. In some embodiments, the second portion contains a higher content of aggregated microorganisms than the first portion before the first portion is recirculated. In some embodiments, the volume of the aqueous suspension that is bled off and recirculated is determined by a computer controlled system comprising sensors. The sensors may comprise turbidity and/or density sensors located at the inlet and exit of the flow path comprising the electrical field. The output from the sensors may be used to control the recirculation of the aqueous suspension based on the sensor output meeting a certain threshold turbidity/density value or change in turbidity/density value.

In some embodiments, the temperature of the aqueous suspension can also be adjusted to control the specific gravity of the water relative to the microorganism. In such embodiments, as the liquid medium (typically composed primarily of water) is heated or cooled, alterations to the liquid medium hydrogen density occurs. This alteration of density can allow a normally less dense material to sink. This alteration, according to some embodiments, also allows easier harvesting of the aggregated microorganism. In a simplified description used to illustrate a heat transfer, according to some embodiments, between the outer walls of the cathode 106 and/or anode 104 and into the liquid medium/biomass during the electrical field application process in a method for harvesting cellular mass and debris from an aqueous solution containing microorganisms is disclosed below. In some embodiments, an applied heating device attaches to the outside wall surfaces of the cathode and the anode, which allows heat transfer to penetrate into the aqueous slurry. According to various embodiments, changes to the specific gravity of the liquid medium, which is mainly composed of water, by heating allows alteration in its compound structures which is mainly due to alterations to the hydrogen element which when altered, lessens the water density. In such embodiments, this density change allows a normally less dense material contained within a water column to sink or, in some embodiments, an aggregated mass of microorganisms to sink. In some embodiments, a heat exchanger device attached to the outside walls of the cathode and the anode, allows heat to transfer out of the electrodes and/or aqueous slurry. In such embodiments, the temperature of the aqueous slurry may be controlled to maintain the microorganisms in a desired condition.

According to embodiments wherein cavitation is used, a micron mixing device, such as a static mixer or other suitable device such as a high throughput stirrer, blade mixer or other mixing device is used to produce a foam layer composed of microbubbles within a liquid medium containing aggregated microorganisms. According to such embodiments, any device suitable for generating microbubbles, however, can be used. In such embodiments, following micronization, the homogenized mixture begins to rise and float upwards. According to such embodiments, as this mixture passes upwards through the liquid column, the aggregated microorganisms freely attach to the rising bubbles, or due to bubble collision, rise to the surface.

Once the foam layer containing these aggregated microorganisms has risen to the top of the liquid column as described with reference to some embodiments, the valuable microorganisms now can be easily skimmed from the surface of the liquid medium and deposited into a harvest tank for later product refinement or other subsequent processes according to various embodiments. According to some embodiments, once the foam layer rises to the top of the secondary tank, the water content trapped within the foam layer generally results in less than 10% of the original liquid mass. Trapped within the foam, according to such embodiments, are the aggregated microorganisms, and the foam is easily floated or skimmed off the surface of the liquid medium. According to various embodiments, this process uses only dewatering of the foam, rather than evaporating the total liquid volume needed for conventional harvest purposes. Such embodiments drastically reduce the dewatering process, energy and/or any chemical inputs while increasing harvest yield and efficiency as well as purity. Further, in such embodiments, water can be recycled to the growth chamber or removed from the system. Likewise, microorganisms can be harvested at any appropriate time, including, for example, daily (batch harvesting) according to various embodiments. In another example or alternative embodiments, microorganisms are harvested continuously (e.g., a slow, constant harvest).

According to various embodiments, once the liquid medium has achieved passage through the electrical field, it is allowed to flow over into a secondary or separation tank (or directly into a device that is located near the bottom of the tank). In such embodiments adapted for dewatering, the secondary tank is a tank containing a micron bubble device or having a micron bubble device attached for desired microorganism separation and dewatering. According to such embodiments, after aggregation, a static mixer or other suitable device (e.g., any static mixer or device which accomplishes a similar effect of producing microbubbles) is used and is located at the lowest point within a secondary or separation tank. When activated, the static mixer produces a series of micron bubbles resulting in a foam layer that develops within the liquid medium. As the liquid medium is continuously pumped through the micro mixer, according to various embodiments, bubbled foam layers radiate outwards through the liquid and begin to rise and float upwards. In such embodiments, the aggregated microorganisms suspended within the liquid medium attach to the micron bubbles floating upwards to the surface.

According to various embodiments, a lower mounting location for a micron mixer when in association with secondary tank and containing a previously treated biomass suspended within a liquid medium. In such embodiments, the liquid medium is then allowed to flow through a lower secondary tank outlet where it is directed to flow through conduit having a directional flow relationship with a liquid pump. Further according to such embodiments, and due to pumping action, the liquid is allowed a single pass through, or to re-circulate through the micron mixer via a micron mixer inlet opening. In embodiments wherein the liquid continues to cyclically flow through micron mixer, microscopic bubbles are increasingly produced relative to each cycle. In such embodiments, micro bubbles radiate outwards within the liquid column, forming a foam layer. As the process continues according to certain embodiments, the composed layer starts to rise upwards towards the surface of the liquid column. In some embodiments, once the foam layer starts its upward journey towards the surface of the liquid column, the pump is shut down, and thus the micronization process is complete. According to such embodiments, this allows all micron bubbles produced at the lower exit point of the micron mixer to rise to the surface, and, as they do, they start collecting aggregated microorganisms in the liquid medium. In various embodiments, the aggregated microorganisms adhere to the micron bubbles floating upwards towards the surface. In some embodiments, pump remains on and continues to produce additional micron bubbles even after the foam layer starts its upward journey. According to such embodiments, the system is allowed to continually process an ongoing flow being introduced to the secondary or separation tank.

A method according to various embodiments for harvesting a foam layer containing approximately ten percent (10%) of the original liquid medium mass/biomass is described below. According to such embodiments, as the foam layer containing the aggregated microorganisms rises to the surface of the liquid medium, a skimming device can be used to remove the foam layer from the surface of liquid medium. In various embodiments, the skimming device located at the surface area of the secondary tank allows the foam layer to be pushed over the side wall of the secondary tank and into a harvesting container where the foam layer is allowed to accumulate for further substance harvesting procedures.

Chemical and Electric Field Aggregation Combination Embodiments

In some embodiments, any of the apparatuses, systems and methods for aggregating microorganisms contained in an aqueous suspension using an electrical field may be combined with a method using a chemical aggregating agent. In some embodiments the chemical aggregating agent facilitates the aggregation of the microorganisms chemically, and in other embodiments the chemical aggregating agent improves the electrical conductivity of the aqueous suspension to facilitate the aggregation of the microorganisms electrically (e.g. change in surface charge). The aggregating agents may include, but are not limited to, salt, alum, aluminum chlorohydrate, aluminum sulfate, calcium oxide calcium hydroxide, iron (III) chloride, iron (II) sulfate, polyacrylamide, polyDADMAC, sodium aluminate, sodium silicate, chitosan, *Moring a oleifera* seeds, papain, strychnos seeds, isinglass, and combinations thereof. Specific binding agents to one or more components of the microorganism may also be used. The chemical aggregating agent may act directly on the microorganism being aggregated or it may enhance the activity of electroaggregation or acoustic aggregation.

Acoustic Energy Embodiments

In addition to the use of electrical energy to aggregate and separate microorganisms in a flowing aqueous culture medium, acoustic energy also provides a chemical free method of inducing concentration and separation of microorganisms in a flowing aqueous culture medium. Instead of using electrical energy to affect the surface charge of the microorganism, electrical energy can be used by a function generator to produce a radio frequency signal which is converted to acoustic energy by transducers. Transducers in contact with the tube or channel through which the aqueous culture medium is flowing form a standing wave of acoustic pressure within the tube by vibrating the tube. The standing wave of acoustic pressure varies the pressure within the tube, creating areas of high pressure and nodes of low or minima pressure. When an aqueous medium comprising microorganisms flow through the standing waves, microorganisms may be pushed towards the minima pressure nodes. By aggregating the microorganisms at the minima pressure nodes, the microorganisms can be concentrated in a consistent location for coagulation, flocculation and/or separation from the medium.

In one exemplary embodiment, an acoustic energy apparatus comprises: a power source, a radio frequency signal (function) generator, at least one transducer in contact with a tube or channel. In some embodiments, the standing wave is created from the combination or superimposing of multiple out of phase acoustic pressure waves from multiple transducers. In some embodiments, the standing wave is created from the combination of superimposing out of phase acoustic pressure waves from a transducer and a reflector. In some embodiments, the transducer creates a wave which travels across diameter of the tube or channel without reflection.

In the embodiments with a standing wave, at least one minima pressure node may be created at the central axis of the tube, off center of the central axis of the tube, or along the walls of the tube. In some embodiments, there is a single minima pressure node, while in other embodiments there are multiple minima pressure nodes. The wavelength of the standing wave in relation to the diameter of the tube or channel will dictate the location and number of the minima pressure node(s). In one non-limiting example, the diameter of the tube or channel is one half the wavelength of the standing wave and produces a minima pressure node at the central axis of the tube or channel. The number of minima nodes will increase as the wavelength decreases. The higher pressure portions of the standing wave push the microorganisms suspended in the liquid medium to the location of the minima pressure nodes.

In some embodiments, a traveling or sweeping wave is used which has minima pressure nodes which move or translate across the liquid medium. The pressure of the wave traveling or sweeping across the diameter of the tube pushes the microorganisms against one surface of the tube. In further embodiments, the direction of the traveling wave may be changed to move the biasing location of the microorganisms to another surface location of the tube.

The liquid and particles in the aqueous culture medium of a different size and/or acoustic impedance than the microorganisms targeted by the acoustic energy will continue to fill the volume of the tube outside of the minima pressure node.

By biasing the location of the targeted microorganisms within the tube, at least one collector or collection inlet can be located in line with the biased location (e.g. center of tube, along one surface of the tube) to receive the microorganisms and separate the microorganisms from the aqueous medium. The collector may comprise a separate inlet located within the tube, or the tube may split into multiple flow paths with at least one of the branches comprising the collector.

The wave characteristics may be manipulated or tuned through the electrical signal power source, the radio frequency (function) generator, a power amplifier, and/or the transducers. The acoustic waves will affect particles differently based on their size and/or acoustic impedance. Acoustic impedance is determined by the particle shape, size, cell wall composition, physiological state, and compressibility. Examples of particles in the aqueous medium that have different sizes and/or acoustic impedances include, but are not limited to: mature microalgae in oil phase; younger microalgae in growth phase; different species of microalgae; extraneous particulate matter; contaminants, predators, and competitors of microalgae such as grazers, rotifers, fungi, bacteria, viruses, cells or parts of living organisms, non-living cell debris, and suspended organic matter. By tuning the characteristics of the wave, particles of different size and/or acoustic impedance may be targeted and biased to a location in a tube. Selectively biasing the particles to a location aids in the removal of the particles from the aqueous medium for further processing of the particles and separates one group of particles from another. The system may be used for positive or negative selection with either the target particles or the non-target particles being removed selectively. While the specification is described as removing the desired aggregated particles from the liquid, it may equally be applied to removing undesired particles/contaminants. As such the liquid may be returned for additional cell growth or further processed to dewater the desired microorganisms or other particles.

The tube may comprise any material with a natural resonance frequency suitable to create standing waves with minima pressure nodes or transmit a traveling wave such as, but not limited to, glass, plastic, metals, crystalline solids, and quartz. In the creation of the standing waves, the entire length of the tube is excited by the transducer in contact with the tube as the acoustic signal produced by the transducer is converted into acoustic radiation pressure. The thickness of the tube may affect the natural resonance frequency of the tube. The flow through the tube may be essentially laminar, and the flow rate may be controlled by pumping, gravity, valves, or the flow path geometry. The tube may have a circular, oval or elipitical, rectangular, or polygonal cross-section.

The at least one transducer is coupled to the tube, and receives a radio frequency signal for conversion into an acoustic energy signal. The at least one transducer may comprise any suitable material for producing an acoustic energy signal from a radio frequency signal such as, but not limited to, piezoceramic, peizosalt, peizopolymer, piezocrystal, magnetostrictive, electromagnetic transducers, and lead zirconate titanate. In some embodiments, multiple transducers may be used to tune the frequency and provide electronic feedback, such as a pair of transducers on opposing sides of the tube or channel. A reflector or reflection membrane may be used with a single transducer to create a standing wave within a tube or channel. The reflector may comprise any material suitable for reflecting acoustic waves such as, but not limited to, mylar, glass mica, and polymers.

The radio frequency signal generator may comprise a function generator. In some embodiments the radio frequency signal produced by the generator is amplified by a power amplifier before transmission to the at least one transducers. The frequencies may range from 10 kHz to 100 MHz. The frequency selected may be dictated by the desired function of the acoustic waves. Low frequencies may be used for the effect of inhibiting cyanobacteria growth in the aqueous medium. Ultrasonic frequencies may also be used for the effect of lysing or disrupting microalgae cells through cavitation induced by acoustic energy. In some embodiments, the frequency will be tuned to aggregate microorganisms at the minima pressure nodes without inhibiting growth or lysing/disrupting the cells through cavitation.

The power may range from 0.05 W to 1 W for the aggregation of microorganisms at the minima pressure nodes without inhibiting growth or lysing/disrupting the cells. In other embodiments, a higher power value may be used to inhibit growth or lyse/disrupt the microorganisms. The power source may provide constant electrical power (such as direct current), oscillating electrical power (such as alternating current), or a pulsed electrical current, including micro-pulses, pico-pulses, and nano-pulses as previous described above. In one exemplary embodiment using pulsed electrical current, the transducer receives pulses of electricity at a frequency higher than the standing wave, resulting in the rapid starting and stopping of the acoustic energy in a high frequency pulse. After traveling a distance through the medium, the high frequency pulse evolves into a demodulated pulse which can excite the desired mode of the standing acoustic wave.

In some embodiments, multiple transducers and collectors may be used in a series configuration along a length of the tube. In further embodiments, the multiple transducers and collectors concentrate the same target particles for collection at multiple points. In other embodiments, the multiple transducers and collectors concentrate different target particles for collection at multiple points. In some embodiments, multiple collectors may be placed at different locations and the standing waves may be adjusted to move the minima pressure nodes to the different locations of the collectors, effectively activating and inactivating the collectors selectively. In some embodiments, a standing wave may be used to concentrate the target particles at a minima pressure node first, and then moved towards a collector using a travelling or sweeping wave second. Additionally, a plurality of tubes which apply acoustic energy to the aqueous medium may be connected in a series or parallel arrangement as described above with the plurality of anode and cathode circuits. The system may be used for positive or negative selection with either the target particles or the non-target particles being removed selectively.

Combination Electroacoustic Embodiments

Figure 20A:
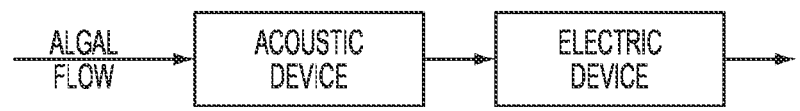
FIGS. 20A-B each show exemplary systems that combine electrical energy and acoustic energy.

In some embodiments, the application of electrical energy, as described above, and acoustic energy can be used in combination in a single system. In one embodiment, the system may switch back and forth between the application of electrical energy and acoustic energy to the aqueous suspension. In one embodiment, as illustrated in FIG. 20A, acoustic energy is applied to the aqueous medium comprising microorganisms first to concentrate a target microorganism at a minima pressure node. The target microorganism is then separated from the aqueous medium by a collector. Next, the separated target microorganisms are subjected to an electrical field to affect the surface charge of the microorganisms to further aggregate the microorganisms into a more cohesive aggregate mass. The aqueous medium not separated by the collector may be diverted for additional use (such as growth medium for a new culture of microorganisms) or recycled through the system for further application of acoustic energy targeting the same microorganism or a different particle. Embodiments using electrical and acoustic energy in combination may provide for the first separation and aggregation of microorganisms of a first characteristic in the aqueous culture medium, such as oil phase microalgae, a first species of microalgae, or a first contaminant/predator/competitor; and then the subsequent separations and aggregations of microorganisms of a different characteristic, such as growth phase microalgae, a second species of microalgae, or a second contaminant/predator/competitor. Embodiments using electrical and acoustic energy in combination provide an efficient method for: selectively separating and aggregating microalgae in different phases within the same culture; selectively separating and aggregating different microalgae species which were co-cultured; selectively cleaning a culture through separating and aggregating various microorganisms, contaminants, predators, and competitors; and selectively cleaning a culture before aggregating the microorganisms. Acoustic energy can also be used to bias the algae to a certain location and then tunable electrodes may be used to apply an electrical field to the algae location in the most energy efficient manner.

Figure 20B:
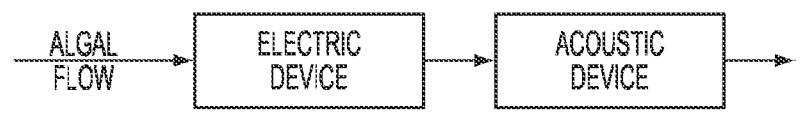

In another embodiment, electrical energy is applied to the aqueous suspension comprising microorganisms first to aggregate the microorganisms into larger aggregate masses, as illustrated in FIG. 20B. Next, acoustic energy is applied to concentrate the aggregate microorganism masses at the minima pressure nodes and separating the larger aggregate masses from the aqueous medium through a collector. The aqueous medium not separated by the collector can be recycled through the system for further application of electrical energy for aggregation. This embodiment provides an efficient method for creating stronger bonds between the microorganisms concentrated at the minima pressure nodes by the acoustic energy.

In some embodiments, a tube with a rectangular shaped cross-section and a pair of plate electrodes with spacers may be joined to form a continuous tube with a rectangular shaped cross-section. In some embodiments, a tube with a circular cross-section and a pair of semi-circular shaped electrodes with spacers may be joined to form a continuous tube with a circular shaped cross-section. The continuous tube may form a single tubular structure with a uniform cross-section for applying both acoustic energy and electrical energy in line in an alternating fashion. In some embodiments an elastomeric spacer joins the acoustic and electric application sections to reduce vibration in the electrical application section and insulate the acoustic application section from an electrical charge.

Figure 21:
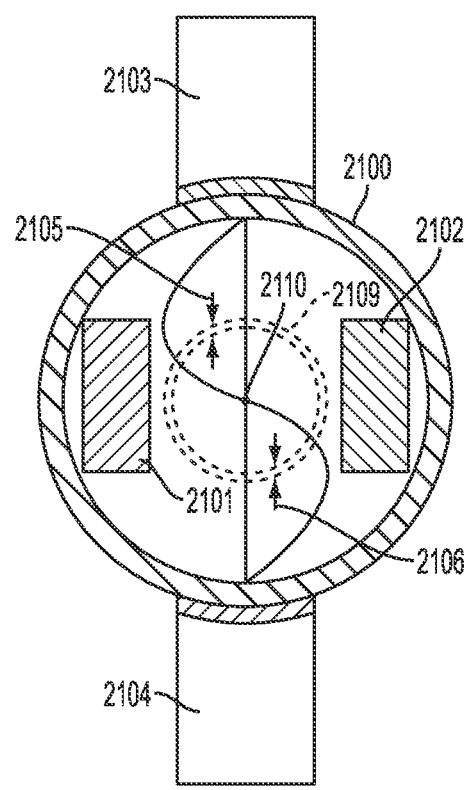
FIG. 21 shows an exemplary embodiment that combines electrical and acoustic energy.

In some embodiments, the electrical and acoustic energy are applied to the aqueous suspension simultaneously. Referring to FIG. 21, a tube 2100 forms the channel for flowing an aqueous suspension comprising microorganisms. The tube 2100 may comprise any suitable material that can be excited by transducers 2103, 2104 to produce a standing wave of acoustic pressure within the interior of the tube. Housed within the tube is an anode 2101 and a cathode 2102 facing each other and running longitudinally through the tube. The anode 2101 and cathode 2102 are spaced to allow a gap between the electrodes in which the minima pressure node 2110 of the acoustic pressure wave is located and the aqueous medium flows through. The transducers 2103, 2104 may create a standing wave within the tube 2100 concurrently with the anode 2101 and cathode 2102 pair producing an electric field within the tube as the aqueous culture suspension comprising microorganisms flows through the tube. The standing wave forms anti-nodes of acoustic pressure wave 2105, 2106.

Figure 22:
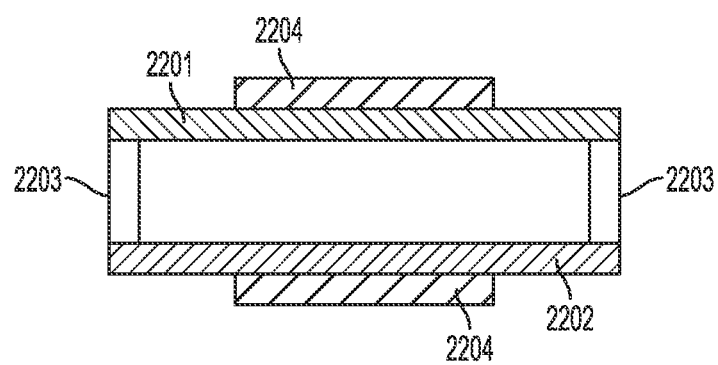
FIG. 22 shows an exemplary embodiment that combines electrical and acoustic energy.

Referring to FIG. 22, the channel for flowing an aqueous solution comprising microorganisms is defined by a spaced anode 2201 and cathode 2202 pair and insulators 2203 as described above in the rectangular channel embodiment above. Transducers 2204 may be coupled to the anode 2201 and cathode 2202 to produce a standing wave of acoustic pressure within the channel by vibrating the anode 2201 and cathode 2202, and form a minima pressure node between the anode 2201 and cathode 2202 concurrently with the anode 2201 and cathode 2202 pair producing an electrical field within the channel as tube as the aqueous culture suspension comprising microorganisms flows through the channel.

Vibration Energy Recovery

In embodiments using acoustic energy, a piezoelectric vibration harvester may be coupled to the tube. The piezoelectric vibration harvester captures some of the mechanical vibration energy used to produce the standing wave and converts the vibration energy into electrical current. The electrical current may be alternating current (AC) or may be converted from AC into direct current (DC). The electrical current may form a power source that can be transmitted wirelessly to sensors, such as flow rate, density, or turbidity sensors on the same aggregating apparatus. The piezoelectric vibration harvesters may be designed or commercially available from companies such as Mide and Perpetuum.

Advantages of using a system with acoustic and electrical energy include: the avoidance of fouling issues common with filters, reduction in the application of shear forces to microorganisms which are common with mechanical systems such as centrifuges, reduction in moving or wear parts that lead to mechanical failure due to friction, and the capability of continuous operation. The application of acoustic and/or electric energy also results in biasing, concentration, and/or aggregation of microalgae in a short time period, such as minutes or seconds. Both the flow rate and biomass concentration of the aqueous medium affect the efficiency of the aggregating methods using acoustic and/or electrical energy, therefore a two pronged approach which uses both methods in various combinations can increase the system efficiency by 1) increasing the size of the particles through electrical aggregation for influence by the acoustic pressure, 2) moving the particles within closer proximity to each other with acoustic pressure for quicker attraction between the particles once the electrical energy alters the surface charge, and 3) aggregating the particles through acoustic pressure into an optimal location for receiving an electrical field. Additionally, biasing particles to a location in the tube or channel away from the surfaces of the tube or channel may prevent biofouling of the tube or channel surfaces. These techniques may be used in combination with any other conventional technique for removing particles, such as filtering, settling, flocculation, centrifugation or other particle aggregation technique. Such may be used either before or after the techniques of the present invention.

It is to be understood that while the invention has been described in conjunction with the preferred specific embodiments thereof and that the foregoing description is intended to illustrate and not limit the scope of the invention. Other aspects, advantages and modifications within the scope of the invention will be apparent to those skilled in the art to which the invention pertains.

What is claimed is:

1. A method of aggregating microorganisms in an aqueous suspension, comprising:

a. flowing an aqueous suspensions comprising microorganisms into an apparatus comprising:

i. at least one electrical conductor comprising a conductive material configured as a cathode;

ii. at least one second electrical conductor comprising a conductive material configured as an anode, wherein the at least one electrical conductor comprising a conductive material configured as a cathode is disposed opposite the at least one second electrical conductor comprising a conductive material configured as an anode;

iii. at least one pair of spaced insulators disposed between the at least one electrical conductor comprising a conductive material configured as a cathode and the at least one electrical conductor comprising a conductive material configured as an anode;

iv. a channel defined between the at least one electrical conductor comprising a conductive material configured as a cathode, the at least one electrical conductor comprising a conductive material configured as an anode, and the pair of at least one pair of insulators, wherein the channel has a length commensurate with the lengths of the at least one cathode and the at least one electrical conductor comprising a conductive material configured as an anode, wherein the channel defines a fluid flow path for the aqueous suspension, and wherein the fluid flow path comprising at least one of a height, a width, and a diameter which varies along at least a portion of a length of the fluid flow path;

v. an electrical power source operably connected to the at least one electrical conductor comprising a conductive material configured as a cathode and the at least one electrical conductor comprising a conductive material configured as an anode, wherein an electric field comprising an intensity is created by applying an electrical current from the electrical power source to the at least one electrical conductor comprising a conductive material configured as a cathode and the at least one electrical conductor comprising a conductive material configured as an anode; and vi. a separation tank in fluid communication downstream of the channel, wherein the separating tank is configured to collect fluid flow from the fluid flow path defined by the channel;

b. flowing the aqueous suspension comprising microorganisms through the channel into a separation tank;

c. applying an electrical current from the electrical power source to the at least one electrical conductor comprising a conductive material configured as a cathode and the at least one electrical conductor comprising a conductive material configured as an anode, wherein an electrical field comprising an intensity is created, wherein the electrical field treats the surface charges of the microorganisms and causes the microorganisms to aggregate with similarly treated microorganisms in the aqueous suspension without disrupting the cell membranes;

d. recirculating at least a portion of the aqueous suspension exiting the fluid flow path of the apparatus back through the apparatus;

e. aggregating the microorganisms in the separation tank; and f. separating the aggregated microorganisms from the aqueous suspension in said separation tank.

2. The method of claim 1, further comprising measuring at least one of density and turbidity of the aqueous suspension exiting the apparatus with a sensor, and transmitting the measurement value to a computer controller.

3. The method of claim 2, wherein the computer controller receives the measurement value from the sensor and adjusts the volume of the portion of the aqueous suspension recirculated through the apparatus based on the measurement value.

4. The method of claim 3, wherein the portion of the aqueous suspension exiting the apparatus which is recirculated to the apparatus is mixed with an untreated volume of aqueous suspension in a continuous aggregation process.

5. The method of claim 3, wherein the electrical power source provides continuous electrical current.

6. The method of claim 3, wherein the electrical power source provides a pulsed electrical current.

7. The method of claim 2, wherein the aqueous suspension exiting the apparatus is recirculated to the apparatus until the measurement value reaches a threshold value in a batch aggregation process.

* * * * *